United States Patent
Chien et al.

(10) Patent No.: US 7,205,329 B2
(45) Date of Patent: Apr. 17, 2007

(54) MODULATORS OF CRTH2 ACTIVITY

(75) Inventors: Yueh-Tyng Chien, Newton, MA (US); G. Todd Milne, Brookline, MA (US); Mark G. Currie, Sterling, MA (US); John Jeffrey Talley, Somerville, MA (US); Brian M. Cali, Arlington, MA (US); Barbara Chen, Braintree, MA (US); Craig Zimmerman, Topsfield, MA (US); Jing Jing Yang, Boxborough, MA (US)

(73) Assignee: Microbia, Inc., Cambridge, MA (US)

( * ) Notice: Subject to any disclaimer, the term of this patent is extended or adjusted under 35 U.S.C. 154(b) by 0 days.

(21) Appl. No.: 11/183,626

(22) Filed: Jul. 18, 2005

(65) Prior Publication Data

US 2006/0135591 A1    Jun. 22, 2006

Related U.S. Application Data

(63) Continuation of application No. 10/951,542, filed on Sep. 27, 2004, now abandoned, which is a continuation-in-part of application No. 10/859,335, filed on Jun. 1, 2004.

(60) Provisional application No. 60/570,620, filed on May 13, 2004, provisional application No. 60/563,589, filed on Apr. 20, 2004, provisional application No. 60/511,792, filed on Oct. 16, 2003, provisional application No. 60/483,935, filed on Jul. 1, 2003, provisional application No. 60/475,204, filed on May 30, 2003.

(51) Int. Cl.
*A61K 31/405*    (2006.01)
*C07D 209/12*    (2006.01)

(52) U.S. Cl. ..................... 514/415; 548/469
(58) Field of Classification Search .............. None
See application file for complete search history.

(56) References Cited

U.S. PATENT DOCUMENTS

| 3,629,284 | A | 12/1971 | Yamamoto | 260/326.13 |
|---|---|---|---|---|
| 5,990,150 | A | 11/1999 | Matsui et al. | 514/415 |
| 6,262,098 | B1 | 7/2001 | Huebner et al. | 514/378 |
| 6,291,505 | B1 | 9/2001 | Huebner et al. | 514/406 |

FOREIGN PATENT DOCUMENTS

| EP | 0620214 | 3/1999 |
|---|---|---|
| EP | 1170594 | 1/2002 |
| GB | 2407318 | 4/2005 |
| WO | WO 00/51685 | 9/2000 |
| WO | WO 01/06537 | 1/2001 |
| WO | WO 03/066046 | 8/2003 |

OTHER PUBLICATIONS

Maguire et al. Bioorganic & Medicinal Chemistry, (2001), 9(3), p. 745-762.*
STN seatch report and abstract, EP620214 Bach et al. (1994).*
STN search report: U.S. Patent 6,684,034 and 6,252,084 (Bach et al.).*

* cited by examiner

*Primary Examiner*—Kamal A. Saeed
*Assistant Examiner*—Yong Chu
(74) *Attorney, Agent, or Firm*—Fish & Richardson P.C.

(57) ABSTRACT

Modulators of the CRTH2 receptor and their use in the treatment of various disorders, including asthma are described.

17 Claims, 2 Drawing Sheets

| chemical name | CRTH2 Agonist Assay # 1 E50 (nM) | CRTH2 Agonist Assay # 2 EC50 (nM) | CRTH2 antagonist assay IC50 (nM) | COX-1 enzyme assay IC50 μm | COX-2 enzyme assay IC50 μm | COX-1 human whole blood assay IC50 μm | COX-2 human whole blood assay IC50 μm |
|---|---|---|---|---|---|---|---|
| [1-(4-chlorobenzoyl)-5-methoxy-2-methyl-1H-indol-3-yl]acetic acid | 52 | 190 | ND | 0.13 | 0.11 | 0.18 | 0.23 |
| [1-(4-chlorobenzoyl)-5-hydroxy-2-methyl-1H-indol-3-yl]acetic acid | 60 | 280 | ND | 10 | 0.2 | 12.9 | 0.51 |
| (1-benzyl-5-hydroxy-2-methyl-1H-indol-3-yl)acetic acid | >100,000 | ND | 2000 | >100 | >10 | ND | ND |
| [1-(4-chlorobenzyl)-5-hydroxy-2-methyl-1H-indol-3-yl]acetic acid | partial agonist at 100μM | ND | 1000 | 60 | >10 | ND | ND |
| 4-[5-(4-methylphenyl)-3-(trifluoromethyl)-1H-pyrazol-1-yl]benzenesulfonamide | >100,000 | >100,000 | ND | 15 | 0.22 | 12.3 | 0.42 |
| [1-(4-chlorobenzoyl)-6-fluoro-5-hydroxy-2-methyl-1H-indol-3-yl]acetic acid | 40 | 50 | ND | 30 | 0.5 | 30.2 | 0.6 |
| [1-(4-chlorobenzoyl)-4-fluoro-5-hydroxy-2-methyl-1H-indol-3-yl]acetic acid | 84 | 74 | ND | >100 | 4.3 | 59.7 | 8 |
| {5-methoxy-2-methyl-1-[4-(trifluoromethyl)benzoyl]-1H-indol-3-yl}acetic acid | >1000 | ND | ND | >100 | 0.2 | 21.5 | 0.6 |
| {6-fluro-5-methoxy-2-methyl-1-[4-(trifluoromethyl)benzoyl]-1H-indol-3-yl}acetic acid | 478 | ND | ND | 76.2 | 0.37 | 27.2 | 0.6 |
| {6-fluoro-5-methoxy-2-methyl-1-[4-(trifluoromethoxy)benzoyl]-1H-indol-3-yl}acetic acid | ~100 | ND | ND | >100 | 0.59 | 41.8 | 0.35 |
| {1-[(5-chloro-2-thienyl)carbonyl]-6-fluoro-5-hydroxy-2-methyl-1H-indol-3-yl}acetic acid | >100,000 | ND | 200-300 | 85 | 0.56 | 36 | 0.86 |
| {1-[(4-difluoromethoxy)benzoyl]-6-fluoro-5-methoxy-2-methyl-1H-indol-3-yl}acetic acid | 450 | ND | ND | 18.1 | 0.1 | 12.2 | 0.19 |
| {1-[(4-bromobenzoyl)-6-fluoro-5-hydroxy-2-methyl-1H-indol-3-yl]acetic acid | 26 | ND | ND | 21.1 | 0.18 | 60.9 | 0.67 |

FIG. 1A

| chemical name | CRTH2 Agonist Assay # 1 EC50 (nM) | CRTH2 Agonist Assay # 2 EC50 (nM) | CRTH2 antagonist assay IC50 (nM) | COX-1 enzyme assay IC50 μm | COX-2 enzyme assay IC50 μm | COX-1 human whole blood assay IC50 μm | COX-2 human whole blood assay IC50 μm |
|---|---|---|---|---|---|---|---|
| [6-fluoro-1-(4-fluorobenzoyl)-5-hydroxy-2-methyl-1H-indol-3-yl]acetic acid | partial agonist at 10μM | ND | <1000 | >100 | 0.18 | 26.6 | 0.63 |
| [6-fluoro-5-hydroxy-2-methyl-1-(2-thienylcarbonyl)-1H-indol-3-yl]acetic acid | >100,000 | ND | <10,000 | 27.3 | 0.23 | 14.5 | 0.2 |
| {1-[4-(difluoromethoxy)benzoyl]-6-fluoro-5-hydroxy-2-methyl-1H-indol-3-yl}acetic acid | 787 | ND | ND | >100 | 0.2 | 71 | 0.85 |
| methyl [1-(4-chlorobenzoyl)-6-fluoro-5-hydroxy-2-methyl-1H-indol-3-yl]acetate | >1000 | ND | >10,000 | 30.1 | 8.38 | ND | ND |
| [6-chloro-1-(4-chlorobenzoyl)-5-methoxy-2-methyl-1H-indol-3-yl]acetic acid | 66 | ND | ND | 20.2 | 0.26 | 14 | 0.43 |
| ethyl [1-(4-chlorobenzoyl)-6-fluoro-5-hydroxy-2-methyl-1H-indol-3-yl]acetate | >1000 | ND | >10,000 | 33 | 5.98 | ND | ND |
| propyl [1-(4-chlorobenzoyl)-6-fluoro-5-hydroxy-2-methyl-1H-indol-3-yl]acetate | >1000 | ND | >10,000 | 28 | 5.79 | ND | ND |
| {6-chloro-1-[4-(difluoromethoxy)benzoyl]-5-methoxy-2-methyl-1H-indol-3-yl}acetic acid | 1000 | ND | ND | >100 | 0.67 | 54.3 | 0.26 |
| Prostaglandin D2 (control) | 5 | 13 | ND | N/A | N/A | N/A | N/A |
| 15R-methyl prostaglandin D2 (control) | 3 | ND | ND | N/A | N/A | N/A | N/A |
| 5-oxo-6,8,11,14-eicosatetraenoic acid (control) | ND | 2.4 | ND | N/A | N/A | N/A | N/A |
| 3-((3R)-3-{[((4-fluorophenyl)sulfonyl]amino}-1,2,3,4-tetrahydro-9H-carbazol-9-yl) propanoic acid (control) | ND | ND | 30-50 | N/A | N/A | N/A | N/A |

FIG. 1B

MODULATORS OF CRTH2 ACTIVITY

This application is a continuation of U.S. application Ser. No. 10/951,542, filed Sep. 27, 2004 now abandoned, which is a continuation-in-part (and claims the benefit of priority under 35 USC 120) of U.S. Ser. No. 10/859,335, filed Jun. 1, 2004, which claims priority to Provisional Application Ser. No. 60/475,204, filed May 30. 2004. and U.S. Ser. No. 10/833,900, filed Jul. 1, 2004, which claims to Provisional Application Ser. No. 60/483,935, filed Jul. 1, 2003, Under 35 USC §119(e)(1), this application claims the benefit of prior U.S. provisional applications; Provisional Application Ser. No. 60/511,792, filed on Oct. 16, 2003; Provisional Application Ser. 60/563,589 filed Apr. 20, 2004 and Provisional Application Ser. No. 60/570,620 filed on May 13, 2004. The disclosure of the prior applications are considered part of (and are incorporated by reference) in the disclosure of this application.

BACKGROUND

CRTH2 is a $G_{\alpha i}$ protein-coupled receptor that is thought to be involved in both mediating $PGD_2$-induced chemoattraction and in activation of specific cell types involved in allergic inflammation. It has been reported that CRTH2 is expressed by Th2 cells, eosinophils and basophils, but not by Th1 cells, B cells or NK cells. (Nagata et al. 1999 *FEBS Letters* 459:195–199).

$PGD_2$ is produced by allergen-activated mast cells and has been implicated in various allergic diseases as a pro-inflammatory mediator, although it may have anti-inflammatory activity in certain situations (Ajuebor et al. 2000 *Am J Physiol Gastrointest Liver Physiol* 279:G238–44). CRTH2 receptor is a high affinity receptor for $PGD_2$ as is DP, a $G_{\alpha S}$ protein-coupled receptor.

CRTH2 agonists activate eosinophils, basophils and Th2 cells in vitro, resulting in induction of actin polymerization, calcium influx, CD11b expression and chemotaxis (Monneret et al 2003 *J Pharmacol Exp Ther* 304:349–55). An in vivo study has demonstrated that injection of a CRTH2 agonist can elicit transient recruitment of eosinophils from bone marrow into the blood (Shichijo 2003 *J Pharmacol Exp Ther* 307:518–525). A genetic study of African American and Chinese cohorts found that polymorphisms in CRTH2 were tightly associated with asthma susceptibility (Huang et al. 2004 *Hum Mol. Genet* 2791). It has been suggested that modulators of CRTH2 may be useful in the prevention and/or treatment of allergic asthma and other allergic disorders (US 2002/0022218 A1 and WO 03/066047).

SUMMARY

The invention features compounds having Formula I and pharmaceutically acceptable salts and polymorphs thereof, as well as pharmaceutical compositions comprising such compounds. The invention also features therapeutic and prophylactic methods involving the administration of such pharmaceutical compositions alone or in combination with one or more other therapeutic agents. The compounds of the invention are modulators of CRTH2 activity, e.g., they are agonists or antagonists of CRTH2. Some compounds may be partial agonists or inverse agonists (inhibitors of basal level activity). Pharmaceutical compositions containing the compounds of the invention are useful for preventing and/or treating a variety of disorders, including, allergic rhinitis, asthma, atopic dermatitis, eosinophilic esophagitis, and other disorders associated with allergic inflammation.

The invention features a compound having the formula:

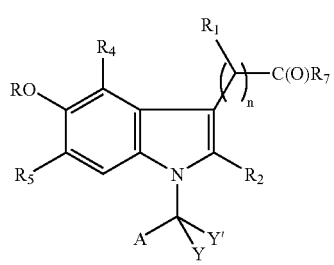

Formula I wherein:

A is

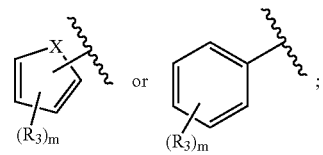

R is H, a $C_1$–$C_3$ alkyl, optionally independently substituted with one or more halogen;

n is 1, 2, 3 or 4;

$R_1$ is H; a $C_1$–$C_6$ alkyl, optionally independently substituted with one or more —OH, —$NH_2$, or halogen; or a $C_1$–$C_6$ alkenyl optionally independently substituted with one or more —OH, —$NH_2$ or halogen;

$R_2$ is H; a $C_1$–$C_6$ alkyl, optionally independently substituted with one or more halogen; or a $C_1$–$C_6$ alkenyl optionally independently substituted with one or more halogen;

$R_3$ is a halogen; —CN; —OH; —SH; a $C_1$–$C_3$ alkyl, optionally independently substituted with one or more halogen; —$OR_{3A}$; —$SR_{3A}$; —$SOR_{3A}$; or —$S(O)_2R_{3A}$, wherein $R_{3A}$ is a $C_1$–$C_3$ alkyl, optionally independently substituted with one or more halogen;

m is 0, 1, 2, 3, 4 or 5;

$R_4$ is H or a halogen;

$R_5$ is H or a halogen;

Y and Y' are both H; Y and Y' taken together are S; or Y and Y' taken together are O;

X is O, S, or —$NR_6$, wherein $R_6$ is a $C_1$–$C_3$ alkyl, optionally independently substituted with one or more halogen; and $R_7$ is —OH, —$OR_{7A}$; or $R_{7A}$, wherein $R_{7A}$ is: H or a $C_1$ to $C_6$ ($C_1$, $C_2$, $C_3$, $C_4$, $C_5$, $C_6$) alkyl, alkenyl, alkynyl, aryl, cycloalkyl, or arylalkyl optionally independently substituted with one or more halogen —OH, —C(O)OH, or —$NH_3$.

In some embodiments: A is

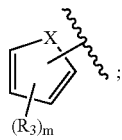

X is S; X is O; X is —NR$_6$; A is

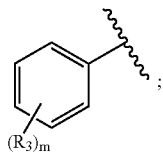

R$_3$ is F; Cl; —CN; —OH; —SH; a C$_1$–C$_3$ alkyl, optionally independently substituted with one or more F or Cl; —OR$_{3A}$; —SR$_{3A}$; —SOR$_{3A}$; or —S(O)$_2$R$_{3A}$, wherein R$_{3A}$ is a C$_1$–C$_3$ alkyl, optionally independently substituted with one or more F or Cl; R$_3$ is F; Cl; —CN; —OH; —SH; a C$_1$–C$_3$ alkyl, optionally independently substituted with one or more F or Cl; and R$_3$ is —OR$_{3A}$; —SR$_{3A}$; —SOR$_{3A}$; or —S(O)$_2$R$_{3A}$, wherein R$_{3A}$ is a C$_1$–C$_3$ alkyl, optionally independently substituted with one or more F or Cl.

In some embodiments, R$_7$ is —OH. In some embodiments R$_7$ is —OR$_{7A}$, wherein R$_{7A}$ is: a C$_1$ to C$_6$ (C$_1$, C$_2$, C$_3$, C$_4$, C$_5$, C$_6$) alkyl, alkenyl, alkynyl, aryl, cycloalkyl, or arylalkyl optionally independently substituted with one or more halogen —OH, —C(O)OH, or —NH$_3$. In some embodiments, R$_7$ is OR$_{7A}$, wherein R$_{7A}$ is: a C$_1$ to C$_6$ (C$_1$, C$_2$, C$_3$, C$_4$, C$_5$, C$_6$) alkyl optionally independently substituted with one or more halogen —OH, —C(O)OH, or —NH$_3$. In some embodiments, in which R$_7$ is —OR$_{7A}$ or R$_{7A}$, the compound is hydrolyzed so that —(O)R$_7$ is converted to —C(O)OH.

In some embodiments, R is H. Many such compound are CRTH2 antagonists. Some are not CRTH2 antagonists In some embodiments, R is a C$_1$–C$_3$ alkyl, optionally independently substituted with one or more halogen. Many such compounds are CRTH2 agonists. Some are not CRTH2 agonists.

In other embodiments, the compound is a CRTH2 agonist; the compound has an EC$_{50}$ for CRTH2 that is less than 20 μM; the compound has an EC$_{50}$ for CRTH2 that is less than 10 μM; and the compound has an EC$_{50}$ for CRTH2 that is less than 5 μM.

In some embodiments, the compound is a CRTH2 antagonist; the compound has an IC$_{50}$ for CRTH2 that is less than 20 μM; the compound has an IC$_{50}$ for CRTH2 that is less than 10 μM; and the compound has an IC$_{50}$ for CRTH2 that is less than 5 μM.

In some embodiments, Y and Y' taken together are S; Y and Y' taken together are O; Y and Y' are both H; R$_4$ is H, F or Cl; R$_5$ is H, F or Cl; R is H, a C$_1$–C$_3$ alkyl, optionally independently substituted with one or more F or Cl.

In some embodiments, R$_1$ is H; a C$_1$–C$_6$ alkyl, optionally independently substituted with one or more —OH, —NH$_2$, or F or Cl; or a C$_1$–C$_6$ alkenyl optionally independently substituted with one or more —OH, —NH$_2$, F or Cl.

In some embodiments R$_2$ is H; a C$_1$–C$_6$ alkyl, optionally independently substituted with one or more F or Cl; or a C$_1$–C$_6$ alkenyl optionally independently substituted with one or more F or Cl.

In some embodiments m is 1, 2, 3, 4 or 5. In some embodiments m is 0, 1, 2 or 3. In some embodiments m is 1, 2 or 3.

Where Y and Y' taken together are O the compounds have the formula:

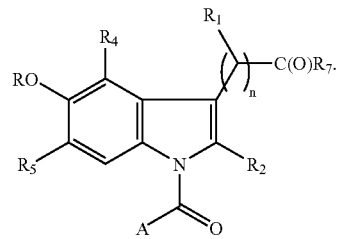

Where Y and Y' taken together are S the compounds have the formula:

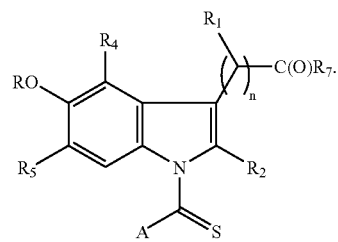

Where Y and Y' are both H the compounds have the formula:

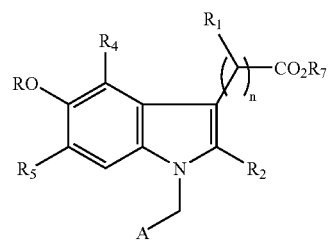

The invention also features a compound having the formula:

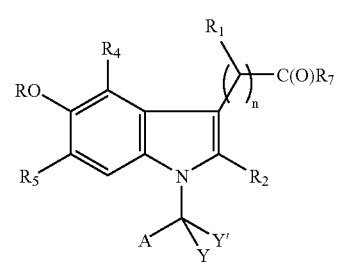

wherein:

A is

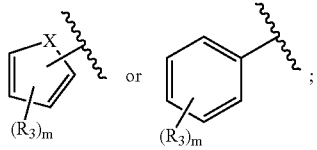

R is H, a $C_1$–$C_3$ alkyl, optionally independently substituted with one or more halogen;

n is 1, 2, 3 or 4;

$R_1$ is H; a $C_1$–$C_6$ alkyl, optionally independently substituted with one or more —OH, —$NH_2$, or halogen; or a $C_1$–$C_6$ alkenyl optionally independently substituted with one or more —OH, —$NH_2$ or halogen;

$R_2$ is H; a $C_1$–$C_6$ alkyl, optionally independently substituted with one or more halogen; or a $C_1$–$C_6$ alkenyl optionally independently substituted with one or more halogen;

$R_3$ is a halogen; —CN; —OH; —SH; a $C_1$–$C_3$ alkyl, optionally independently substituted with one or more halogen; —$OR_{3A}$; —$SR_{3A}$; —$SOR_{3A}$; or —$S(O)_2R_{3A}$, wherein $R_{3A}$ is a $C_1$–$C_3$ alkyl, optionally independently substituted with one or more halogen;

m is 0, 1, 2, 3, 4, or 5;

$R_4$ is H or a halogen;

$R_5$ is H or a halogen;

Y and Y' are both H; Y and Y' taken together are S; or Y and Y' taken together are O;

X is O, S, or —$NR_6$, wherein $R_6$ is a $C_1$–$C_3$ alkyl, optionally independently substituted with one or more halogen; and $R_7$ is —OH, —$OR_{7A}$; or $R_{7A}$, wherein $R_{7A}$ is: H or a $C_1$ to $C_6$ ($C_1$, $C_2$, $C_3$, $C_4$, $C_5$, $C_6$) alkyl, alkenyl, alkynyl, aryl, cycloalkyl, or arylalkyl optionally independently substituted with one or more halogen —OH, —C(O)OH, or —$NH_3$;

provided that if A is

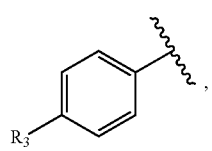

n is 1, $R_1$ is H, Y is O, $R_2$ is —$CH_3$, $R_4$ is H, $R_5$ is H and R is —$CH_3$, then $R_3$ is not: Cl, H, F or —$CF_3$; further provided that if A is

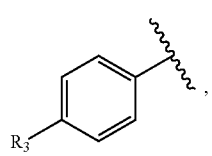

n is 1, $R_1$ is H, Y is O, $R_2$ is —$CH_3$, $R_4$ is H, $R_5$ is H, R is H, then $R_3$ is not H; further provided that when A is

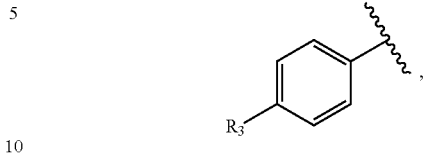

n is 1, $R_1$ is H, Y is O, $R_2$ is —$CH_3$, $R_4$ is F, $R_5$ is H, R is —$CH_3$, $R_3$ is not H; and further provided that when A is

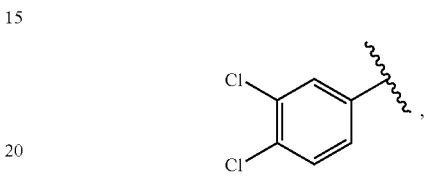

n is 1, $R_1$ is H, Y is O, $R_2$ is —$CH_3$, $R_4$ is H, $R_5$ is H, then R is not H.

In some embodiments, $R_3$ is selected from: F, Cl, Br, OH, —$OCH_3$, —$OCH_2CH_3$, —$OCF_2H$, —$OCF_3$, —$OCF_2CF_3$, —$OCF_2CF_2H$, —$CH_3$, —$CF_2H$, —$CF_3$, —$SCH_3$, —$SCF_2H$, $SCF_3$, —$SCF_2CF_3$, —$SCF_2CF_2H$, and —CN.

In some embodiments, A is

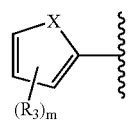

and A is

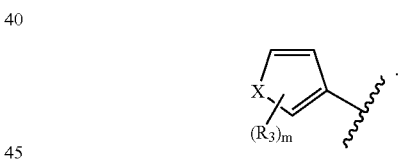

In some embodiments m is 1, 2, 3, 4 or 5. In some embodiments m is 0, 1, 2 or 3. In some embodiments m is 1, 2 or 3.

The invention also includes a pharmaceutical composition comprising a compound of claim having Formula I and a pharmaceutically acceptable carrier.

The invention also includes a method for treating a disorder characterized by imbalance of the Th1/Th2 ratio towards Th1, the method comprising administering a compound having Formula I. In some embodiments, the disorder is selected from: rheumatoid arthritis, Type I diabetes, psoriasis, gastritis, irritable bowel disorder, multiple sclerosis, painless throiditis, lupus, and Crohn's Disease.

The invention also includes a method for treating a disorder characterized by imbalance of the Th1/Th2 ratio towards Th2, the method comprising administering a compound having Formula I. In some embodiments, the disorder is selected from: asthma, atopic dermatitis, allergic rhinitis, allergy, and Grave's Disease.

The invention features a method for treating a disorder selected from asthma, allergic rhinitis, atopic dermatitis, eosinophilic esophagitis, and other disorders associated with allergic inflammation, the method comprising administering a compound having Formula I. In some embodiments, the compound is a CRTH2 antagonists. In some embodiments, R is H. In some embodiments, the method further comprises administering a second compound that is an anti-inflammatory agent.

The invention also features a method for treating a disorder characterized by undesirable activation of Th1 cells, the method comprising administering compound of Formula I.

The invention also features a method for treating a disorder characterized by undesirable activation of Th2 cells, the method comprising administering compound of Formula I.

In some embodiments, the disorder is selected from: rheumatoid arthritis, Type I diabetes, psoriasis, gastritis, irritable bowel disorder, multiple sclerosis, painless thyroiditis, lupus, and Crohn's Disease. In other embodiments, the disorder is selected from: asthma, atopic dermatitis, allergic rhinitis, allergy, and Grave's Disease.

The invention also features a method for modulating CRTH2 activity in a patient, the method comprising administering a compound having Formula I to a patient. In some embodiments, the compound is a CRTH2 agonist. In others it is an antagonist. In some embodiments, R is H. In others R is a $C_1$–$C_3$ alkyl, optionally independently substituted with one or more halogen.

The invention features a pharmaceutical composition comprising a compound of the invention (or a salt thereof, e.g., a TRIS or other salt thereof) and a pharmaceutically acceptable carrier.

The invention also features a method for treating a patient for a disorder characterized by an increased level of a cytokine produced by Th2 cells, e.g., a disorder characterized by increased (e.g., undesirably increased) IL-4, IL-10 and/or IL-13 in a patient, the method comprising administering to the patient a CRTH2 modulator described herein.

The invention also features a method for treating a patient for a disorder characterized by an increased level of a cytokine produced by Th1 cells, e.g., a disorder characterized by increased (e.g., undesirably increased) interferon-γ in a patient, the method comprising administering to the patient a CRTH2 modulator described herein.

The invention also features a method for increasing the Th1 cell/Th2 cell ratio in a patient, the method comprising administering to the patient a CRTH2 modulator, e.g., a CRTH2 antagonist.

The invention also features a method for decreasing the Th1 cell/Th2 cell ratio in a patient, the method comprising administering to the patient a CRTH2 modulator, e.g., a CRTH2 agonist.

In some embodiments the CRTH2 modulators are also inhibitors of cyclooxygenase-1 (COX-1) and/or cyclooxygenase-2 (COX-2). Among compounds that inhibit COX-2 and/or COX-1, those that are those that selective for COX-2 are preferred. Thus, in some embodiments: the compound exhibits an $IC_{50}$ for COX-2 that is at least 20,000; 10,000; 1,000; 500; 100; 50; or 25 μM, and have an $IC_{50}$ for COX-1 that is even greater than the $IC_{50}$ for COX-2. In some embodiments the COX-1 $IC_{50}$ for a compound is at least 2, 5, 10, 25, 50, 100, 500, 1000 or more times the COX-1 $IC_{50}$ for indomethacin in the same assay.

Some desirable compound having the structure of Formula I have an $EC_{50}$ for human CRTH2 that is less than 20, 10, 2.0, 1.5, 1.0, 0.5, 0.4, 0.3, 0.2, 0.1, 0.08, 0.06, 0.04, 0.02, or 0.01 μM.

Some desirable compound having the structure of Formula I have an $IC_{50}$ for human CRTH2 that is less than 20, 10, 2.0, 1.5, 1.0, 0.5, 0.4, 0.3, 0.2, 0.1, 0.08, 0.06, 0.04, 0.02, or 0.01 μM.

Exemplary Compounds

Among the compounds of Formula I are the following compounds wherein m is 1 to 5, preferably 1, 2, or 3 and R3 is selected from: a halogen (preferably F or Cl), OH, —OCH$_3$, —OCH$_2$CH$_3$, —OCF$_2$H, —OCF$_3$, —OCF$_2$CF$_3$, —OCF$_2$CF$_2$H, —CH$_3$, —CF$_2$H, —CF$_3$, —SCH$_3$, —SCF$_2$H, —SCF$_3$, —SCF$_2$CF$_3$, —SCF$_2$CF$_2$H, and —CN. The invention also includes variations of the following compounds in which —CO$_2$H (i.e., —C(O)OH) is replaced by —C(O)R$_7$ wherein R$_7$ is —OH, —OR$_{7A}$; or R$_{7A}$; wherein R$_{7A}$ is: H or a $C_1$ to $C_6$ ($C_1$, $C_2$, $C_3$, $C_4$, $C_5$, $C_6$) alkyl, alkenyl, alkynyl, aryl, cycloalkyl, or arylalkyl optionally independently substituted with one or more halogen —OH, —C(O) OH, or —NH$_3$.

(1-benzyl-6-fluoro-5-hydroxy-2-methyl-1H-indol-3-yl) acetic acid derivatives having the formula:

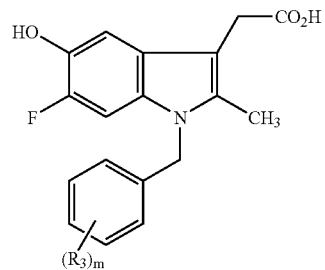

including:

(1-benzyl-6-fluoro-5-hydroxy-2-methyl-1H-indol-3-yl)acetic acid;

[6-fluoro-1-(4-fluorobenzyl)-5-hydroxy-2-methyl-1H-indol-3-yl]acetic acid;

[1-(4-chlorobenzyl)-6-fluoro-5-hydroxy-2-methyl-1H-indol-3-yl]acetic acid;

[1-(4-bromobenzyl)-6-fluoro-5-hydroxy-2-methyl-1H-indol-3-yl]acetic acid;

[6-fluoro-5-hydroxy-1-(4-hydroxybenzyl)-2-methyl-1H-indol-3-yl]acetic acid;

[6-fluoro-5-hydroxy-1-(4-methoxybenzyl)-2-methyl-1H-indol-3-yl]acetic acid;

[1-(4-ethoxybenzyl)-6-fluoro-5-hydroxy-2-methyl-1H-indol-3-yl]acetic acid;

{1-[4-(difluoromethoxy)benzyl]-6-fluoro-5-hydroxy-2-methyl-1H-indol-3-yl}acetic acid;

{6-fluoro-5-hydroxy-2-methyl-1-[4-(trifluoromethoxy)benzyl]-1H-indol-3-yl}acetic acid;

{6-fluoro-5-hydroxy-2-methyl-1-[4-(1,1,2,2-tetrafluoroethoxy)benzyl]-1H-indol-3-yl}acetic acid;

{6-fluoro-5-hydroxy-2-methyl-1-[4-(pentafluoroethoxy)benzyl]-1H-indol-3-yl}acetic acid;

[6-fluoro-5-hydroxy-2-methyl-1-(4-methylbenzyl)-1H-indol-3-yl]acetic acid;

{1-[4-(difluoromethyl)benzyl]-6-fluoro-5-hydroxy-2-methyl-1H-indol-3-yl}acetic acid;

{6-fluoro-5-hydroxy-2-methyl-1-[4-(trifluoromethyl)benzyl]-1H-indol-3-yl}acetic acid;
(1-{4-[(difluoromethyl)thio]benzyl}-6-fluoro-5-hydroxy-2-methyl-1H-indol-3-yl)acetic acid;
(6-fluoro-5-hydroxy-2-methyl-1-{4-[(trifluoromethyl)thio]benzyl}-1H-indol-3-yl)acetic acid;
(6-fluoro-5-hydroxy-2-methyl-1-{4-[(1,1,2,2-tetrafluoroethyl)thio]benzyl}-1H-indol-3-yl)acetic acid;
(6-fluoro-5-hydroxy-2-methyl-1-{4-[(pentafluoroethyl)thio]benzyl}-1H-indol-3-yl)acetic acid; and
[1-(4-cyanobenzyl)-6-fluoro-5-hydroxy-2-methyl-1H-indol-3-yl]acetic acid.
(1-benzoyl-6-fluoro-5-hydroxy-2-methyl-1H-indol-3-yl)acetic acid derivatives having the formula:

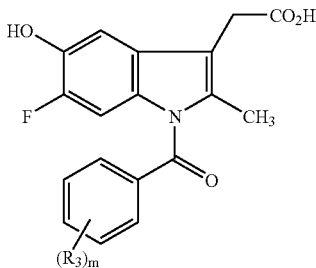

including:
(1-benzoyl-6-fluoro-5-hydroxy-2-methyl-1H-indol-3-yl)acetic acid;
[6-fluoro-1-(4-fluorobenzoyl)-5-hydroxy-2-methyl-1H-indol-3-yl]acetic acid;
[1-(4-chlorobenzoyl)-6-fluoro-5-hydroxy-2-methyl-1H-indol-3-yl]acetic acid;
[1-(4-bromobenzoyl)-6-fluoro-5-hydroxy-2-methyl-1H-indol-3-yl]acetic acid;
[6-fluoro-5-hydroxy-1-(4-hydroxybenzoyl)-2-methyl-1H-indol-3-yl]acetic acid;
[6-fluoro-5-hydroxy-1-(4-methoxybenzoyl)-2-methyl-1H-indol-3-yl]acetic acid;
[1-(4-ethoxybenzoyl)-6-fluoro-5-hydroxy-2-methyl-1H-indol-3-yl]acetic acid;
{1-[4-(difluoromethoxy)benzoyl]-6-fluoro-5-hydroxy-2-methyl-1H-indol-3-yl}acetic acid;
{6-fluoro-5-hydroxy-2-methyl-1-[4-(trifluoromethoxy)benzoyl]-1H-indol-3-yl}acetic acid;
{6-fluoro-5-hydroxy-2-methyl-1-[4-(1,1,2,2-tetrafluoroethoxy)benzoyl]-1H-indol-3-yl}acetic acid;
{6-fluoro-5-hydroxy-2-methyl-1-[4-(pentafluoroethoxy)benzoyl]-1H-indol-3-yl}acetic acid;
[6-fluoro-5-hydroxy-2-methyl-1-(4-methylbenzoyl)-1H-indol-3-yl]acetic acid;
{1-[4-(difluoromethyl)benzoyl]-6-fluoro-5-hydroxy-2-methyl-1H-indol-3-yl}acetic acid;
{6-fluoro-5-hydroxy-2-methyl-1-[4-(trifluoromethyl)benzoyl]-1H-indol-3-yl}acetic acid;
(1-{4-[(difluoromethyl)thio]benzoyl}-6-fluoro-5-hydroxy-2-methyl-1H-indol-3-yl)acetic acid;
(6-fluoro-5-hydroxy-2-methyl-1-{4-[(trifluoromethyl)thio]benzoyl}-1H-indol-3-yl)acetic acid;
(6-fluoro-5-hydroxy-2-methyl-1-{4-[(1,1,2,2-tetrafluoroethyl)thio]benzoyl}-1H-indol-3-yl)acetic acid;
(6-fluoro-5-hydroxy-2-methyl-1-{4-[(pentafluoroethyl)thio]benzoyl}-1H-indol-3-yl)acetic acid; and
[1-(4-cyanobenzoyl)-6-fluoro-5-hydroxy-2-methyl-1H-indol-3-yl]acetic acid.
[6-fluoro-5-hydroxy-2-methyl-1-(thien-2-ylcarbonyl)-1H-indol-3-yl]acetic acid derivatives having the formula:

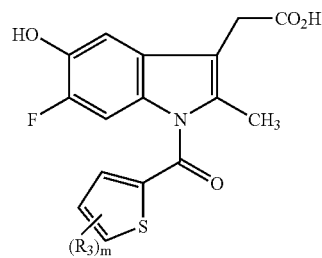

including:
[6-fluoro-5-hydroxy-2-methyl-1-(thien-2-ylcarbonyl)-1H-indol-3-yl]acetic acid;
{6-fluoro-1-[(5-fluorothien-2-yl)carbonyl]-5-hydroxy-2-methyl-1H-indol-3-yl}acetic acid;
{1-[(5-chlorothien-2-yl)carbonyl]-6-fluoro-5-hydroxy-2-methyl-1H-indol-3-yl}acetic acid;
{1-[(5-bromothien-2-yl)carbonyl]-6-fluoro-5-hydroxy-2-methyl-1H-indol-3-yl}acetic acid;
{6-fluoro-5-hydroxy-1-[(5-hydroxythien-2-yl)carbonyl]-2-methyl-1H-indol-3-yl}acetic acid;
{6-fluoro-5-hydroxy-1-[(5-methoxythien-2-yl)carbonyl]-2-methyl-1H-indol-3-yl}acetic acid;
{1-[(5-ethoxythien-2-yl)carbonyl]-6-fluoro-5-hydroxy-2-methyl-1H-indol-3-yl}acetic acid;
(1-{[5-(difluoromethoxy)thien-2-yl]carbonyl}-6-fluoro-5-hydroxy-2-methyl-1H-indol-3-yl)acetic acid;
(6-fluoro-5-hydroxy-2-methyl-1-{[5-(trifluoromethoxy)thien-2-yl]carbonyl}-1H-indol-3-yl)acetic acid;
(6-fluoro-5-hydroxy-2-methyl-1-{[5-(pentafluoroethoxy)thien-2-yl]carbonyl}-1H-indol-3-yl)acetic acid;
(6-fluoro-5-hydroxy-2-methyl-1-{[5-(1,1,2,2-tetrafluoroethoxy)thien-2-yl]carbonyl}-1H-indol-3-yl)acetic acid;
{6-fluoro-5-hydroxy-2-methyl-1-[(5-methylthien-2-yl)carbonyl]-1H-indol-3-yl}acetic acid;
(1-{[5-(difluoromethyl)thien-2-yl]carbonyl}-6-fluoro-5-hydroxy-2-methyl-1H-indol-3-yl)acetic acid;
(6-fluoro-5-hydroxy-2-methyl-1-{[5-(trifluoromethyl)thien-2-yl]carbonyl}-1H-indol-3-yl)acetic acid;
(6-fluoro-5-hydroxy-2-methyl-1-{[5-(methylthio)thien-2-yl]carbonyl}-1H-indol-3-yl)acetic acid;
[1-({5-[(difluoromethyl)thio]thien-2-yl}carbonyl)-6-fluoro-5-hydroxy-2-methyl-1H-indol-3-yl]acetic acid;
[6-fluoro-5-hydroxy-2-methyl-1-({5-[(trifluoromethyl)thio]thien-2-yl}carbonyl)-1H-indol-3-yl]acetic acid;
[6-fluoro-5-hydroxy-2-methyl-1-({5-[(pentafluoroethyl)thio]thien-2-yl}carbonyl)-1H-indol-3-yl]acetic acid;
[6-fluoro-5-hydroxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-6-fluoro-5-hydroxy-2-methyl-1H-indol-3-yl}acetic acid

[6-fluoro-5-hydroxy-2-methyl-1-(thien-2-ylmethyl)-1H-indol-3-yl]acetic acid derivatives having the formula:

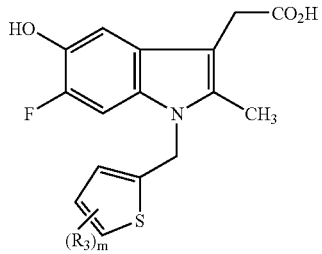

including:
[6-fluoro-5-hydroxy-2-methyl-1-(thien-2-ylmethyl)-1H-indol-3-yl]acetic acid;
{6-fluoro-1-[(5-fluorothien-2-yl)methyl]-5-hydroxy-2-methyl-1H-indol-3-yl}acetic acid;
{1-[(5-chlorothien-2-yl)methyl]-6-fluoro-5-hydroxy-2-methyl-1H-indol-3-yl}acetic acid;
{1-[(5-bromothien-2-yl)methyl]-6-fluoro-5-hydroxy-2-methyl-1H-indol-3-yl}acetic acid;
{6-fluoro-5-hydroxy-1-[(5-hydroxythien-2-yl)methyl]-2-methyl-1H-indol-3-yl}acetic acid;
{6-fluoro-5-hydroxy-1-[(5-methoxythien-2-yl)methyl]-2-methyl-1H-indol-3-yl}acetic acid;
{1[(5-ethoxythien-2-yl)methyl]-6-fluoro-5-hydroxy-2-methyl-1H-indol-3-yl}acetic acid;
(1-{[5-(difluoromethoxy)thien-2-yl]methyl}-6-fluoro-5-hydroxy-2-methyl-1H-indol-3-yl)acetic acid;
(6-fluoro-5-hydroxy-2-methyl-1-{[5-(trifluoromethoxy)thien-2-yl]methyl}-1H-indol-3-yl)acetic acid;
(6-fluoro-5-hydroxy-2-methyl-1-{[5-(pentafluoroethoxy)thien-2-yl]methyl}-1H-indol-3-yl)acetic acid;
(6-fluoro-5-hydroxy-2-methyl-1-{[5-(1,1,2,2-tetrafluoroethoxy)thien-2-yl]methyl}-1H-indol-3-yl)acetic acid;
{6-fluoro-5-hydroxy-2-methyl-1-[(5-methylthien-2-yl)methyl]-1H-indol-3-yl}acetic acid
(1-{[5-(difluoromethyl)thien-2-yl]methyl}-6-fluoro-5-hydroxy-2-methyl-1H-indol-3-yl)acetic acid;
(6-fluoro-5-hydroxy-2-methyl-1-{[5-(trifluoromethyl)thien-2-yl]methyl}-1H-indol-3-yl)acetic acid;
(6-fluoro-5-hydroxy-2-methyl-1-{[5-(methylthio)thien-2-yl]methyl}-1H-indol-3-yl)acetic acid;
[1-({5-[(difluoromethyl)thio]thien-2-yl}methyl)-6-fluoro-5-hydroxy-2-methyl-1H-indol-3-yl]acetic acid;
[6-fluoro-5-hydroxy-2-methyl-1-({5-[(trifluoromethyl)thio]thien-2-yl}methyl)-1H-indol-3-yl]acetic acid;
[6-fluoro-5-hydroxy-2-methyl-1-({5-[(pentafluoroethyl)thio]thien-2-yl}methyl)-1H-indol-3-yl]acetic acid;
[6-fluoro-5-hydroxy-2-methyl-1-({5-[(1,1,2,2-tetrafluoroethyl)thio]thien-2-yl}methyl)-1H-indol-3-yl]acetic acid; and
{1-[(5-cyanothien-2-yl)methyl]-6-fluoro-5-hydroxy-2-methyl-1H-indol-3-yl}acetic acid.

[6-fluoro-5-hydroxy-2-methyl-1-(thien-3-ylmethyl)-1H-indol-3-yl]acetic acid derivatives having the formula:

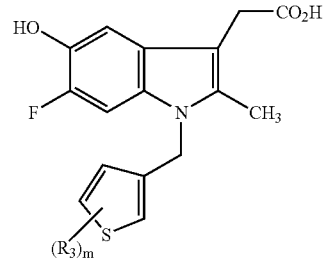

including:
[6-fluoro-5-hydroxy-2-methyl-1-(thien-3-ylmethyl)-1H-indol-3-yl]acetic acid;
{6-fluoro-1-[(5-fluorothien-3-yl)methyl]-5-hydroxy-2-methyl-1H-indol-3-yl}acetic acid;
{1-[(5-chlorothien-3-yl)methyl]-6-fluoro-5-hydroxy-2-methyl-1H-indol-3-yl}acetic acid;
{1-[(5-bromothien-3-yl)methyl]-6-fluoro-5-hydroxy-2-methyl-1H-indol-3-yl}acetic acid;
{6-fluoro-5-hydroxy-1-[(5-hydroxythien-3-yl)methyl]-2-methyl-1H-indol-3-yl}acetic acid;
{6-fluoro-5-hydroxy-1-[(5-methoxythien-3-yl)methyl]-2-methyl-1H-indol-3-yl}acetic acid;
{1-[(5-ethoxythien-3-yl)methyl]-6-fluoro-5-hydroxy-2-methyl-1H-indol-3-yl}acetic acid
(1-{[5-(difluoromethoxy)thien-3-yl]methyl}-6-fluoro-5-hydroxy-2-methyl-1H-indol-3-yl)acetic acid;
(6-fluoro-5-hydroxy-2-methyl-1-{[5-(trifluoromethoxy)thien-3-yl]methyl}-1H-indol-3-yl)acetic acid;
(6-fluoro-5-hydroxy-2-methyl-1-{[5-(pentafluoroethoxy)thien-3-yl]methyl}-1H-indol-3-yl)acetic acid;
(6-fluoro-5-hydroxy-2-methyl-1-{[5-(1,1,2,2-tetrafluoroethoxy)thien-3-yl]methyl}-1H-indol-3-yl)acetic acid;
{6-fluoro-5-hydroxy-2-methyl-1-[(5-methylthien-3-yl)methyl]-1H-indol-3-yl}acetic acid
(1-{[5-(difluoromethyl)thien-3-yl]methyl}-6-fluoro-5-hydroxy-2-methyl-1H-indol-3-yl)acetic acid;
(6-fluoro-5-hydroxy-2-methyl-1-{[5-(trifluoromethyl)thien-3-yl]methyl}-1H-indol-3-yl)acetic acid;
(6-fluoro-5-hydroxy-2-methyl-1-{[5-(methylthio)thien-3-yl]methyl}-1H-indol-3-yl)acetic acid;
[1-({5-[(difluoromethyl)thio]thien-3-yl}methyl)-6-fluoro-5-hydroxy-2-methyl-1H-indol-3-yl]acetic acid;
[6-fluoro-5-hydroxy-2-methyl-1-({5-[(trifluoromethyl)thio]thien-3-yl}methyl)-1H-indol-3-yl]acetic acid;
[6-fluoro-5-hydroxy-2-methyl-1-({5-[(pentafluoroethyl)thio]thien-3-yl}methyl)-1H-indol-3-yl]acetic acid;
[6-fluoro-5-hydroxy-2-methyl-1-({5-[(1,1,2,2-tetrafluoroethyl)thio]thien-3-yl}methyl)-1H-indol-3-yl]acetic acid; and
{1-[(5-cyanothien-3-yl)methyl]-6-fluoro-5-hydroxy-2-methyl-1H-indol-3-yl}acetic acid.
[6-fluoro-5-hydroxy-2-methyl-1-(thien-3-ylcarbonyl)-1H-indol-3-yl]acetic acid derivatives having the formula:

13

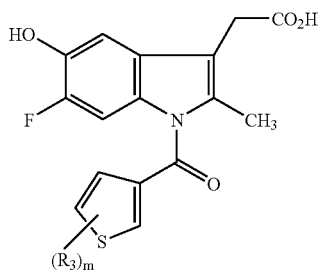

including:

[6-fluoro-5-hydroxy-2-methyl-1-(thien-3-ylcarbonyl)-1H-indol-3-yl]acetic acid;

{6-fluoro-1-[(5-fluorothien-3-yl)carbonyl]-5-hydroxy-2-methyl-1H-indol-3-yl}acetic acid;

{1-[(5-chlorothien-3-yl)carbonyl]-6-fluoro-5-hydroxy-2-methyl-1H-indol-3-yl}acetic acid;

{1-[(5-bromothien-3-yl)carbonyl]-6-fluoro-5-hydroxy-2-methyl-1H-indol-3-yl}acetic acid;

{6-fluoro-5-hydroxy-1-[(5-hydroxythien-3-yl)carbonyl]-2-methyl-1H-indol-3-yl}acetic acid;

{6-fluoro-5-hydroxy-1-[(5-methoxythien-3-yl)carbonyl]-2-methyl-1H-indol-3-yl}acetic acid;

{1-[(5-ethoxythien-3-yl)carbonyl]-6-fluoro-5-hydroxy-2-methyl-1H-indol-3-yl}acetic acid;

(1-{[5-(difluoromethoxy)thien-3-yl]carbonyl}-6-fluoro-5-hydroxy-2-methyl-1H-indol-3-yl)acetic acid;

(6-fluoro-5-hydroxy-2-methyl-1-{[5-(trifluoromethoxy)thien-3-yl]carbonyl}-1H-indol-3-yl)acetic acid;

(6-fluoro-5-hydroxy-2-methyl-1-{[5-(pentafluoroethoxy)thien-3-yl]carbonyl}-1H-indol-3-yl)acetic acid;

(6-fluoro-5-hydroxy-2-methyl-1-{[5-(1,1,2,2-tetrafluoroethoxy)thien-3-yl]carbonyl}-1H-indol-3-yl)acetic acid;

{6-fluoro-5-hydroxy-2-methyl-1-[(5-methylthien-3-yl)carbonyl]-1H-indol-3-yl}acetic acid;

(1-{[5-(difluoromethyl)thien-3-yl]carbonyl}-6-fluoro-5-hydroxy-2-methyl-1H-indol-3-yl)acetic acid;

(6-fluoro-5-hydroxy-2-methyl-1-{[5-(trifluoromethyl)thien-3-yl]carbonyl}-1H-indol-3-yl)acetic acid;

(6-fluoro-5-hydroxy-2-methyl-1-{[5-(methylthio)thien-3-yl]carbonyl}-1H-indol-3-yl)acetic acid;

[1-({5-[(difluoromethyl)thio]thien-3-yl}carbonyl)-6-fluoro-5-hydroxy-2-methyl-1H-indol-3-yl]acetic acid;

[6-fluoro-5-hydroxy-2-methyl-1-({5-[(trifluoromethyl)thio]thien-3-yl}carbonyl)-1H-indol-3-yl]acetic acid;

[6-fluoro-5-hydroxy-2-methyl-1-({5-[(pentafluoroethyl)thio]thien-3-yl}carbonyl)-1H-indol-3-yl]acetic acid;

[6-fluoro-5-hydroxy-2-methyl-1-({5-[(1,1,2,2-tetrafluoroethyl)thio]thien-3-yl}carbonyl)-1H-indol-3-yl]acetic acid; and {1-[(5-cyanothien-3-yl)carbonyl]-6-fluoro-5-hydroxy-2-methyl-1H-indol-3-yl}acetic acid.

(1-benzyl-6-chloro-5-hydroxy-2-methyl-1H-indol-3-yl)acetic acid derivatives having the formula:

14

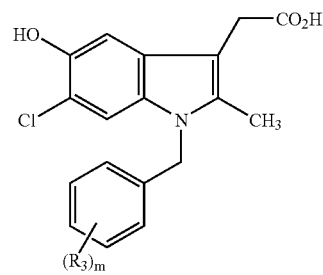

including:

(1-benzyl-6-chloro-5-hydroxy-2-methyl-1H-indol-3-yl)acetic acid;

[6-chloro-1-(4-fluorobenzyl)-5-hydroxy-2-methyl-1H-indol-3-yl]acetic acid;

[1-(4-chlorobenzyl)-6-chloro-5-hydroxy-2-methyl-1H-indol-3-yl]acetic acid;

[1-(4-bromobenzyl)-6-chloro-5-hydroxy-2-methyl-1H-indol-3-yl]acetic acid;

[6-chloro-5-hydroxy-1-(4-hydroxybenzyl)-2-methyl-1H-indol-3-yl]acetic acid;

[6-chloro-5-hydroxy-1-(4-methoxybenzyl)-2-methyl-1H-indol-3-yl]acetic acid

[1-(4-ethoxybenzyl)-6-chloro-5-hydroxy-2-methyl-1H-indol-3-yl]acetic acid;

{1-[4-(difluoromethoxy)benzyl]-6-chloro-5-hydroxy-2-methyl-1H-indol-3-yl}acetic acid;

{6-chloro-5-hydroxy-2-methyl-1-[4-(trifluoromethoxy)benzyl]-1H-indol-3-yl}acetic acid;

{6-chloro-5-hydroxy-2-methyl-1-[4-(1,1,2,2-tetrafluoroethoxy)benzyl]-1H-indol-3-yl}acetic acid;

{6-chloro-5-hydroxy-2-methyl-1-[4-(pentafluoroethoxy)benzyl]-1H-indol-3-yl}acetic acid;

[6-chloro-5-hydroxy-2-methyl-1-(4-methylbenzyl)-1H-indol-3-yl]acetic acid;

{1-[4-(difluoromethyl)benzyl]-6-chloro-5-hydroxy-2-methyl-1H-indol-3-yl}acetic acid;

{6-chloro-5-hydroxy-2-methyl-1-[4-(trifluoromethyl)benzyl]-1H-indol-3-yl}acetic acid;

(1-{4-[(difluoromethyl)thio]benzyl}-6-chloro-5-hydroxy-2-methyl-1H-indol-3-yl)acetic acid;

(6-chloro-5-hydroxy-2-methyl-1-{4-[(trifluoromethyl)thio]benzyl}-1H-indol-3-yl)acetic acid;

(6-chloro-5-hydroxy-2-methyl-1-{4-[(1,1,2,2-tetrafluoroethyl)thio]benzyl}-1H-indol-3-yl)acetic acid;

(6-chloro-5-hydroxy-2-methyl-1-{4-[(pentafluoroethyl)thio]benzyl}-1H-indol-3-yl)acetic acid; and

[1-(4-cyanobenzyl)-6-chloro-5-hydroxy-2-methyl-1H-indol-3-yl]acetic acid.

(1-benzoyl-6-chloro-5-hydroxy-2-methyl-1H-indol-3-yl) acetic acid derivatives having the formula:

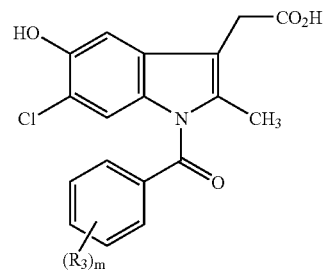

including:

(1-benzoyl-6-chloro-5-hydroxy-2-methyl-1H-indol-3-yl)acetic acid;
[6-chloro-1-(4-fluorobenzoyl)-5-hydroxy-2-methyl-1H-indol-3-yl]acetic acid;
[1-(4-chlorobenzoyl)-6-chloro-5-hydroxy-2-methyl-1H-indol-3-yl]acetic acid;
[1-(4-bromobenzoyl)-6-chloro-5-hydroxy-2-methyl-1H-indol-3-yl]acetic acid;
[6-chloro-5-hydroxy-1-(4-hydroxybenzoyl)-2-methyl-1H-indol-3-yl]acetic acid;
[6-chloro-5-hydroxy-1-(4-methoxybenzoyl)-2-methyl-1H-indol-3-yl]acetic acid;
[1-(4-ethoxybenzoyl)-6-chloro-5-hydroxy-2-methyl-1H-indol-3-yl]acetic acid;
{1-[4-(difluoromethoxy)benzoyl]-6-chloro-5-hydroxy-2-methyl-1H-indol-3-yl}acetic acid;
{6-chloro-5-hydroxy-2-methyl-1-[4-(trifluoromethoxy)benzoyl]-1H-indol-3-yl}acetic acid;
{6-chloro-5-hydroxy-2-methyl-1-[4-(1,1,2,2-tetrafluoroethoxy)benzoyl]-1H-indol-3-yl}acetic acid;
{6-chloro-5-hydroxy-2-methyl-1-[4-(pentafluoroethoxy)benzoyl]-1H-indol-3-yl}acetic acid;
[6-chloro-5-hydroxy-2-methyl-1-(4-methylbenzoyl)-1H-indol-3-yl]acetic acid;
{1-[4-(difluoromethyl)benzoyl]-6-chloro-5-hydroxy-2-methyl-1H-indol-3-yl}acetic acid;
{6-chloro-5-hydroxy-2-methyl-1-[4-(trifluoromethyl)benzoyl]-1H-indol-3-yl}acetic acid;
(1-{4-[(difluoromethyl)thio]benzoyl}-6-chloro-5-hydroxy-2-methyl-1H-indol-3-yl)acetic acid;
(6-chloro-5-hydroxy-2-methyl-1-{4-[(trifluoromethyl)thio]benzoyl}-1H-indol-3-yl)acetic acid;
(6-chloro-5-hydroxy-2-methyl-1-{4-[(1,1,2,2-tetrafluoroethyl)thio]benzoyl}-1H-indol-3-yl)acetic acid;
(6-chloro-5-hydroxy-2-methyl-1-{4-[(pentafluoroethyl)thio]benzoyl}-1H-indol-3-yl)acetic acid; and
[1-(4-cyanobenzoyl)-6-chloro-5-hydroxy-2-methyl-1H-indol-3-yl]acetic acid.

[6-chloro-5-hydroxy-2-methyl-1-(thien-3-ylmethyl)-1H-indol-3-yl]acetic acid derivatives having the formula:

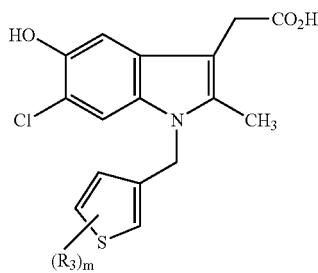

including:
[6-chloro-5-hydroxy-2-methyl-1-(thien-3-ylmethyl)-1H-indol-3-yl]acetic acid;
{6-chloro-1-[(5-fluorothien-3-yl)methyl]-5-hydroxy-2-methyl-1H-indol-3-yl}acetic acid;
{1-[(5-chlorothien-3-yl)methyl]-6-chloro-5-hydroxy-2-methyl-1H-indol-3-yl}acetic acid;
{1-[(5-bromothien-3-yl)methyl]-6-chloro-5-hydroxy-2-methyl-1H-indol-3-yl}acetic acid;
{6-chloro-5-hydroxy-1-[(5-hydroxythien-3-yl)methyl]-2-methyl-1H-indol-3-yl}acetic acid;
{6-chloro-5-hydroxy-1-[(5-methoxythien-3-yl)methyl]-2-methyl-1H-indol-3-yl}acetic acid;
{1-[(5-ethoxythien-3-yl)methyl]-6-chloro-5-hydroxy-2-methyl-1H-indol-3-yl}acetic acid;
(1-{[5-(difluoromethoxy)thien-3-yl]methyl}-6-chloro-5-hydroxy-2-methyl-1H-indol-3-yl)acetic acid;
(6-chloro-5-hydroxy-2-methyl-1-{[5-(trifluoromethoxy)thien-3-yl]methyl}-1H-indol-3-yl)acetic acid;
(6-chloro-5-hydroxy-2-methyl-1-{[5-(pentafluoroethoxy)thien-3-yl]methyl}-1H-indol-3-yl)acetic acid;
(6-chloro-5-hydroxy-2-methyl-1-{[5-(1,1,2,2-tetrafluoroethoxy)thien-3-yl]methyl}-1H-indol-3-yl)acetic acid;
{6-chloro-5-hydroxy-2-methyl-1-[(5-methylthien-3-yl)methyl]-1H-indol-3-yl}acetic acid;
(1-{[5-(difluoromethyl)thien-3-yl]methyl}-6-chloro-5-hydroxy-2-methyl-1H-indol-3-yl)acetic acid;
(6-chloro-5-hydroxy-2-methyl-1-{[5-(trifluoromethyl)thien-3-yl]methyl}-1H-indol-3-yl)acetic acid;
(6-chloro-5-hydroxy-2-methyl-1-{[5-(methylthio)thien-3-yl]methyl}-1H-indol-3-yl)acetic acid;
[1-({5-[(difluoromethyl)thio]thien-3-yl}methyl)-6-chloro-5-hydroxy-2-methyl-1H-indol-3-yl]acetic acid;
[6-chloro-5-hydroxy-2-methyl-1-({5-[(trifluoromethyl)thio]thien-3-yl}methyl)-1H-indol-3-yl]acetic acid;
[6-chloro-5-hydroxy-2-methyl-1-({5-[(pentafluoroethyl)thio]thien-3-yl}methyl)-1H-indol-3-yl]acetic acid;
[6-chloro-5-hydroxy-2-methyl-1-({5-[(1,1,2,2-tetrafluoroethyl)thio]thien-3-yl}methyl)-1H-indol-3-yl]acetic acid; and
{1-[(5-cyanothien-3-yl)methyl]-6-chloro-5-hydroxy-2-methyl-1H-indol-3-yl}acetic acid.

[6-chloro-5-hydroxy-2-methyl-1-(thien-3-ylcarbonyl)-1H-indol-3-yl]acetic acid derivatives having the formula:

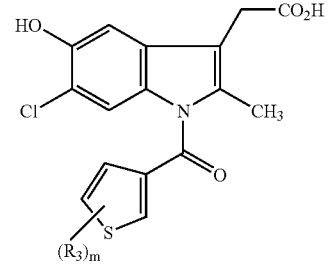

including:
[6-chloro-5-hydroxy-2-methyl-1-(thien-3-ylcarbonyl)-1H-indol-3-yl]acetic acid;
{6-chloro-1-[(5-fluorothien-3-yl)carbonyl]-5-hydroxy-2-methyl-1H-indol-3-yl}acetic acid;
{1-[(5-chlorothien-3-yl)carbonyl]-6-chloro-5-hydroxy-2-methyl-1H-indol-3-yl}acetic acid;
{1-[(5-bromothien-3-yl)carbonyl]-6-chloro-5-hydroxy-2-methyl-1H-indol-3-yl}acetic acid;
{6-chloro-5-hydroxy-1-[(5-hydroxythien-3-yl)carbonyl]-2-methyl-1H-indol-3-yl}acetic acid;
{6-chloro-5-hydroxy-1-[(5-methoxythien-3-yl)carbonyl]-2-methyl-1H-indol-3-yl}acetic acid;
{1-[(5-ethoxythien-3-yl)carbonyl]-6-chloro-5-hydroxy-2-methyl-1H-indol-3-yl}acetic acid;
(1-{[5-(difluoromethoxy)thien-3-yl]carbonyl}-6-chloro-5-hydroxy-2-methyl-1H-indol-3-yl)acetic acid;
(6-chloro-5-hydroxy-2-methyl-1-{[5-(trifluoromethoxy)thien-3-yl]carbonyl}-1H-indol-3-yl)acetic acid;

(6-chloro-5-hydroxy-2-methyl-1-{[5-(pentafluoroethoxy)thien-3-yl]carbonyl}-1H-indol-3-yl)acetic acid;
(6-chloro-5-hydroxy-2-methyl-1-{[5-(1,1,2,2-tetrafluoroethoxy)thien-3-yl]carbonyl}-1H-indol-3-yl)acetic acid;
{6-chloro-5-hydroxy-2-methyl-1-[(5-methylthien-3-yl)carbonyl]-1H-indol-3-yl}acetic acid;
(1-{[5-(difluoromethyl)thien-3-yl]carbonyl}-6-chloro-5-hydroxy-2-methyl-1H-indol-3-yl)acetic acid;
(6-chloro-5-hydroxy-2-methyl-1-{[5-(trifluoromethyl)thien-3-yl]carbonyl}-1H-indol-3-yl)acetic acid;
(6-chloro-5-hydroxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-chloro-5-hydroxy-2-methyl-1H-indol-3-yl]acetic acid;
[6-chloro-5-hydroxy-2-methyl-1-({5-[(trifluoromethyl)thio]thien-3-yl}carbonyl)-1H-indol-3-yl]acetic acid;
[6-chloro-5-hydroxy-2-methyl-1-(({5-[(pentafluoroethyl)thio]thien-3-yl}carbonyl)-1H-indol-3-yl]acetic acid;
[6-chloro-5-hydroxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-6-chloro-5-hydroxy-2-methyl-1H-indol-3-yl}acetic acid.
[6-chloro-5-hydroxy-2-methyl-1-(thien-2-ylmethyl)-1H-indol-3-yl]acetic acid derivatives having the formula:

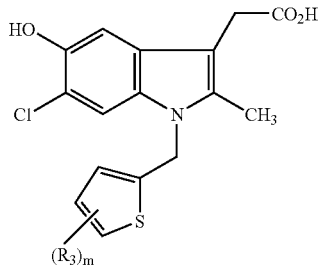

including:
[6-chloro-5-hydroxy-2-methyl-1-(thien-2-ylmethyl)-1H-indol-3-yl]acetic acid;
{6-chloro-1-[(5-fluorothien-2-yl)methyl]-5-hydroxy-2-methyl-1H-indol-3-yl}acetic acid;
{1-[(5-chlorothien-2-yl)methyl]-6-chloro-5-hydroxy-2-methyl-1H-indol-3-yl}acetic acid;
{1-[(5-bromothien-2-yl)methyl]-6-chloro-5-hydroxy-2-methyl-1H-indol-3-yl}acetic acid;
{6-chloro-5-hydroxy-1-[(5-hydroxythien-2-yl)methyl]-2-methyl-1H-indol-3-yl}acetic acid;
{6-chloro-5-hydroxy-1-[(5-methoxythien-2-yl)methyl]-2-methyl-1H-indol-3-yl}acetic acid;
{1-[(5-ethoxythien-2-yl)methyl]-6-chloro-5-hydroxy-2-methyl-1H-indol-3-yl}acetic acid;
(1-{[5-(difluoromethoxy)thien-2-yl]methyl}-6-chloro-5-hydroxy-2-methyl-1H-indol-3-yl)acetic acid;
(6-chloro-5-hydroxy-2-methyl-1-{[5-(trifluoromethoxy)thien-2-yl]methyl}-1H-indol-3-yl)acetic acid;
(6-chloro-5-hydroxy-2-methyl-1-{[5-(pentafluoroethoxy)thien-2-yl]methyl}-1H-indol-3-yl)acetic acid;
(6-chloro-5-hydroxy-2-methyl-1-{[5-(1,1,2,2-tetrafluoroethoxy)thien-2-yl]methyl}-1H-indol-3-yl)acetic acid;
{6-chloro-5-hydroxy-2-methyl-1-[(5-methylthien-2-yl)methyl]-1H-indol-3-yl}acetic acid;
(1-{[5-(difluoromethyl)thien-2-yl]methyl}-6-chloro-5-hydroxy-2-methyl-1H-indol-3-yl)acetic acid;
(6-chloro-5-hydroxy-2-methyl-1-{[5-(trifluoromethyl)thien-2-yl]methyl}-1H-indol-3-yl)acetic acid;
(6-chloro-5-hydroxy-2-methyl-1-{[5-(methylthio)thien-2-yl]methyl}-1H-indol-3-yl)acetic acid;
[1-({5-[(difluoromethyl)thio]thien-2-yl}methyl)-6-chloro-5-hydroxy-2-methyl-1H-indol-3-yl]acetic acid;
[6-chloro-5-hydroxy-2-methyl-1-({5-[(trifluoromethyl)thio]thien-2-yl}methyl)-1H-indol-3-yl]acetic acid;
[6-chloro-5-hydroxy-2-methyl-1-({5-[(pentafluoroethyl)thio]thien-2-yl}methyl)-1H-indol-3-yl]acetic acid;
[6-chloro-5-hydroxy-2-methyl-1-({5-[(1,1,2,2-tetrafluoroethyl)thio]thien-2-yl}methyl)-1H-indol-3-yl]acetic acid; and
{1-[(5-cyanothien-2-yl)methyl]-6-chloro-5-hydroxy-2-methyl-1H-indol-3-yl}acetic acid.
[6-chloro-5-hydroxy-2-methyl-1-(thien-2-ylcarbonyl)-1H-indol-3-yl]acetic acid derivatives having the formula:

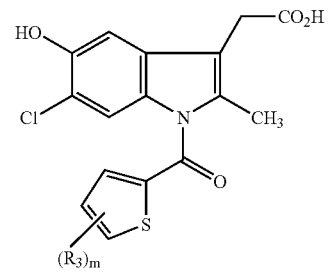

including:
[6-chloro-5-hydroxy-2-methyl-1-(thien-2-ylcarbonyl)-1H-indol-3-yl]acetic acid;
{6-chloro-1-[(5-fluorothien-2-yl)carbonyl]-5-hydroxy-2-methyl-1H-indol-3-yl}acetic acid;
{1-[(5-chlorothien-2-yl)carbonyl]-6-chloro-5-hydroxy-2-methyl-1H-indol-3-yl}acetic acid;
{1-[(5-bromothien-2-yl)carbonyl]-6-chloro-5-hydroxy-2-methyl-1H-indol-3-yl}acetic acid;
{6-chloro-5-hydroxy-1-[(5-hydroxythien-2-yl)carbonyl]-2-methyl-1H-indol-3-yl}acetic acid;
{6-chloro-5-hydroxy-1-[(5-methoxythien-2-yl)carbonyl]-2-methyl-1H-indol-3-yl}acetic acid;
{1-[(5-ethoxythien-2-yl)carbonyl]-6-chloro-5-hydroxy-2-methyl-1H-indol-3-yl}acetic acid;
(1-{[5-(difluoromethoxy)thien-2-yl]carbonyl}-6-chloro-5-hydroxy-2-methyl-1H-indol-3-yl)acetic acid;
(6-chloro-5-hydroxy-2-methyl-1-{[5-(trifluoromethoxy)thien-2-yl]carbonyl}-1H-indol-3-yl)acetic acid;
(6-chloro-5-hydroxy-2-methyl-1-{[5-(pentafluoroethoxy)thien-2-yl]carbonyl}-1H-indol-3-yl)acetic acid;
(6-chloro-5-hydroxy-2-methyl-1-{[5-(1,1,2,2-tetrafluoroethoxy)thien-2-yl]carbonyl}-1H-indol-3-yl)acetic acid;
{6-chloro-5-hydroxy-2-methyl-1-[(5-methylthien-2-yl)carbonyl]-1H-indol-3-yl}acetic acid;
(1-{[5-(difluoromethyl)thien-2-yl]carbonyl}-6-chloro-5-hydroxy-2-methyl-1H-indol-3-yl)acetic acid;
(6-chloro-5-hydroxy-2-methyl-1-{[5-(trifluoromethyl)thien-2-yl]carbonyl}-1H-indol-3-yl)acetic acid;
(6-chloro-5-hydroxy-2-methyl-1-{[5-(methylthio)thien-2-yl]carbonyl}-1H-indol-3-yl)acetic acid;

[1-({5-[(difluoromethyl)thio]thien-2-yl}carbonyl)-6-chloro-5-hydroxy-2-methyl-1H-indol-3-yl]acetic acid;
[6-chloro-5-hydroxy-2-methyl-1-({5-[(trifluoromethyl)thio]thien-2-yl}carbonyl)-1H-indol-3-yl]acetic acid;
[6-chloro-5-hydroxy-2-methyl-1-({5-[(pentafluoroethyl)thio]thien-2-yl}carbonyl)-1H-indol-3-yl]acetic acid;
[6-chloro-5-hydroxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-6-chloro-5-hydroxy-2-methyl-1H-indol-3-yl}acetic acid.

(1-benzyl-6-chloro-5-methoxy-2-methyl-1H-indol-3-yl) acetic acid derivatives having the formula:

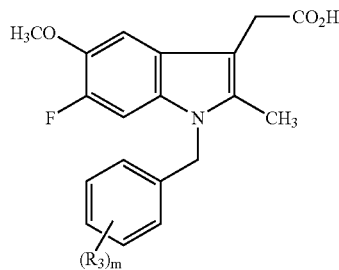

including:
(1-benzyl-6-fluoro-5-methoxy-2-methyl-1H-indol-3-yl)acetic acid;
[6-fluoro-1-(4-fluorobenzyl)-5-methoxy-2-methyl-1H-indol-3-yl]acetic acid;
[1-(4-chlorobenzyl)-6-fluoro-5-methoxy-2-methyl-1H-indol-3-yl]acetic acid;
[1-(4-bromobenzyl)-6-fluoro-5-methoxy-2-methyl-1H-indol-3-yl]acetic acid;
[6-fluoro-5-methoxy-1-(4-hydroxybenzyl)-2-methyl-1H-indol-3-yl]acetic acid;
[6-fluoro-5-methoxy-1-(4-methoxybenzyl)-2-methyl-1H-indol-3-yl]acetic acid;
[1-(4-ethoxybenzyl)-6-fluoro-5-methoxy-2-methyl-1H-indol-3-yl]acetic acid;
{1-[4-(difluoromethoxy)benzyl]-6-fluoro-5-methoxy-2-methyl-1H-indol-3-yl}acetic acid;
{6-fluoro-5-methoxy-2-methyl-1-[4-(trifluoromethoxy)benzyl]-1H-indol-3-yl}acetic acid;
{6-fluoro-5-methoxy-2-methyl-1-[4-(1,1,2,2-tetrafluoroethoxy)benzyl]-1H-indol-3-yl}acetic acid;
{6-fluoro-5-methoxy-2-methyl-1-[4-(pentafluoroethoxy)benzyl]-1H-indol-3-yl}acetic acid;
[6-fluoro-5-methoxy-2-methyl-1-(4-methylbenzyl)-1H-indol-3-yl]acetic acid;
{1-[4-(difluoromethyl)benzyl]-6-fluoro-5-methoxy-2-methyl-1H-indol-3-yl}acetic acid;
{6-fluoro-5-methoxy-2-methyl-1-[4-(trifluoromethyl)benzyl]-1H-indol-3-yl}acetic acid;
(1-{4-[(difluoromethyl)thio]benzyl}-6-fluoro-5-methoxy-2-methyl-1H-indol-3-yl)acetic acid;
(6-fluoro-5-methoxy-2-methyl-1-{4-[(trifluoromethyl)thio]benzyl}-1H-indol-3-yl)acetic acid;
(6-fluoro-5-methoxy-2-methyl-1-{4-[(1,1,2,2-tetrafluoroethyl)thio]benzyl}-1H-indol-3-yl)acetic acid;
(6-fluoro-5-methoxy-2-methyl-1-{4-[(pentafluoroethyl)thio]benzyl}-1H-indol-3-yl)acetic acid; and
[1-(4-cyanobenzyl)-6-fluoro-5-methoxy-2-methyl-1H-indol-3-yl]acetic acid.

(1-benzoyl-6-fluoro-5-methoxy-2-methyl-1H-indol-3-yl) acetic acid derivatives having the formula:

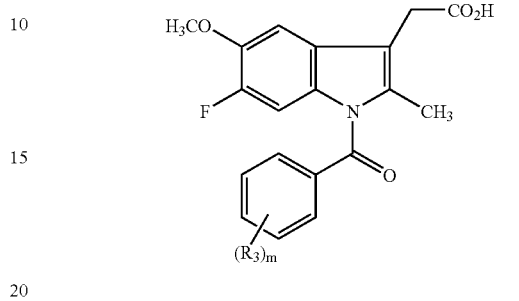

including:
(1-benzoyl-6-fluoro-5-methoxy-2-methyl-1H-indol-3-yl)acetic acid;
[6-fluoro-1-(4-fluorobenzoyl)-5-methoxy-2-methyl-1H-indol-3-yl]acetic acid;
[1-(4-chlorobenzoyl)-6-fluoro-5-methoxy-2-methyl-1H-indol-3-yl]acetic acid;
[1-(4-bromobenzoyl)-6-fluoro-5-methoxy-2-methyl-1H-indol-3-yl]acetic acid;
[6-fluoro-5-methoxy-1-(4-hydroxybenzoyl)-2-methyl-1H-indol-3-yl]acetic acid;
[6-fluoro-5-methoxy-1-(4-methoxybenzoyl)-2-methyl-1H-indol-3-yl]acetic acid;
[1-(4-ethoxybenzoyl)-6-fluoro-5-methoxy-2-methyl-1H-indol-3-yl]acetic acid;
{1-[4-(difluoromethoxy)benzoyl]-6-fluoro-5-methoxy-2-methyl-1H-indol-3-yl}acetic acid;
{6-fluoro-5-methoxy-2-methyl-1-[4-(trifluoromethoxy)benzoyl]-1H-indol-3-yl}acetic acid;
{6-fluoro-5-methoxy-2-methyl-1-[4-(1,1,2,2-tetrafluoroethoxy)benzoyl]-1H-indol-3-yl}acetic acid;
{6-fluoro-5-methoxy-2-methyl-1-[4-(pentafluoroethoxy)benzoyl]-1H-indol-3-yl}acetic acid;
[6-fluoro-5-methoxy-2-methyl-1-(4-methylbenzoyl)-1H-indol-3-yl]acetic acid;
{1-[4-(difluoromethyl)benzoyl]-6-fluoro-5-methoxy-2-methyl-1H-indol-3-yl}acetic acid;
{6-fluoro-5-methoxy-2-methyl-1-[4-(trifluoromethyl)benzoyl]-1H-indol-3-yl}acetic acid;
(1-{4-[(difluoromethyl)thio]benzoyl}-6-fluoro-5-methoxy-2-methyl-1H-indol-3-yl)acetic acid;
(6-fluoro-5-methoxy-2-methyl-1-{4-[(trifluoromethyl)thio]benzoyl}-1H-indol-3-yl)acetic acid;
(6-fluoro-5-methoxy-2-methyl-1-{4-[(1,1,2,2-tetrafluoroethyl)thio]benzoyl}-1H-indol-3-yl)acetic acid;
(6-fluoro-5-methoxy-2-methyl-1-{4-[(pentafluoroethyl)thio]benzoyl}-1H-indol-3-yl)acetic acid; and
[1-(4-cyanobenzoyl)-6-fluoro-5-methoxy-2-methyl-1H-indol-3-yl]acetic acid.

(1-benzyl-6-chloro-5-methoxy-2-methyl-1H-indol-3-yl) acetic acid derivatives having the formula:

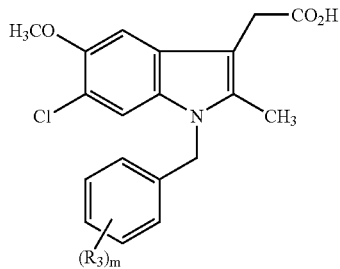

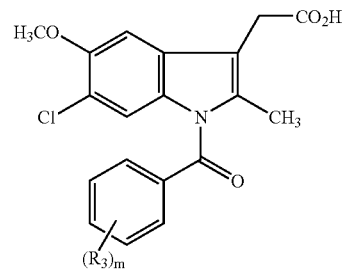

including:
(1-benzyl-6-chloro-5-methoxy-2-methyl-1H-indol-3-yl) acetic acid;
[6-chloro-1-(4-fluorobenzyl)-5-methoxy-2-methyl-1H-indol-3-yl]acetic acid;
[1-(4-chlorobenzyl)-6-chloro-5-methoxy-2-methyl-1H-indol-3-yl]acetic acid;
[1-(4-bromobenzyl)-6-chloro-5-methoxy-2-methyl-1H-indol-3-yl]acetic acid;
[6-chloro-5-methoxy-1-(4-hydroxybenzyl)-2-methyl-1H-indol-3-yl]acetic acid;
[6-chloro-5-methoxy-1-(4-methoxybenzyl)-2-methyl-1H-indol-3-yl]acetic acid;
[1-(4-ethoxybenzyl)-6-chloro-5-methoxy-2-methyl-1H-indol-3-yl]acetic acid;
{1-[4-(difluoromethoxy)benzyl]-6-chloro-5-methoxy-2-methyl-1H-indol-3-yl}acetic acid;
{6-chloro-5-methoxy-2-methyl-1-[4-(trifluoromethoxy)benzyl]-1H-indol-3-yl}acetic acid;
{6-chloro-5-methoxy-2-methyl-1-[4-(1,1,2,2-tetrafluoroethoxy)benzyl]-1H-indol-3-yl}acetic acid;
{6-chloro-5-methoxy-2-methyl-1-[4-(pentafluoroethoxy)benzyl]-1H-indol-3-yl}acetic acid;
[6-chloro-5-methoxy-2-methyl-1-(4-methylbenzyl)-1H-indol-3-yl]acetic acid;
{1-[4-(difluoromethyl)benzyl]-6-chloro-5-methoxy-2-methyl-1H-indol-3-yl}acetic acid;
{6-chloro-5-methoxy-2-methyl-1-[4-(trifluoromethyl)benzyl]-1H-indol-3-yl}acetic acid;
(1-{4-[(difluoromethyl)thio]benzyl}-6-chloro-5-methoxy-2-methyl-1H-indol-3-yl)acetic acid;
(6-chloro-5-methoxy-2-methyl-1-{4-[(trifluoromethyl)thio]benzyl}-1H-indol-3-yl)acetic acid;
(6-chloro-5-methoxy-2-methyl-1-{4-[(1,1,2,2-tetrafluoroethyl)thio]benzyl}-1H-indol-3-yl)acetic acid;
(6-chloro-5-methoxy-2-methyl-1-{4-[(pentafluoroethyl)thio]benzyl}-1H-indol-3-yl)acetic acid; and
[1-(4-cyanobenzyl)-6-chloro-5-methoxy-2-methyl-1H-indol-3-yl]acetic acid.
(1-benzoyl-6-chloro-5-methoxy-2-methyl-1H-indol-3-yl) acetic acid derivatives having the formula:

including:
(1-benzoyl-6-chloro-5-methoxy-2-methyl-1H-indol-3-yl) acetic acid;
[6-chloro-1-(4-fluorobenzoyl)-5-methoxy-2-methyl-1H-indol-3-yl]acetic acid;
[1-(4-chlorobenzoyl)-6-chloro-5-methoxy-2-methyl-1H-indol-3-yl]acetic acid;
[1-(4-bromobenzoyl)-6-chloro-5-methoxy-2-methyl-1H-indol-3-yl]acetic acid;
[6-chloro-5-methoxy-1-(4-hydroxybenzoyl)-2-methyl-1H-indol-3-yl]acetic acid;
[6-chloro-5-methoxy-1-(4-methoxybenzoyl)-2-methyl-1H-indol-3-yl]acetic acid;
[1-(4-ethoxybenzoyl)-6-chloro-5-methoxy-2-methyl-1H-indol-3-yl]acetic acid;
{1-[4-(difluoromethoxy)benzoyl]-6-chloro-5-methoxy-2-methyl-1H-indol-3-yl}acetic acid;
{6-chloro-5-methoxy-2-methyl-1-[4-(trifluoromethoxy)benzoyl]-1H-indol-3-yl}acetic acid;
{6-chloro-5-methoxy-2-methyl-1-[4-(1,1,2,2-tetrafluoroethoxy)benzoyl]-1H-indol-3-yl}acetic acid;
{6-chloro-5-methoxy-2-methyl-1-[4-(pentafluoroethoxy)benzoyl]-1H-indol-3-yl}acetic acid;
[6-chloro-5-methoxy-2-methyl-1-(4-methylbenzoyl)-1H-indol-3-yl]acetic acid;
{1-[4-(difluoromethyl)benzoyl]-6-chloro-5-methoxy-2-methyl-1H-indol-3-yl}acetic acid;
{6-chloro-5-methoxy-2-methyl-1-[4-(trifluoromethyl)benzoyl]-1H-indol-3-yl}acetic acid;
(1-{4-[(difluoromethyl)thio]benzoyl}-6-chloro-5-methoxy-2-methyl-1H-indol-3-yl)acetic acid;
(6-chloro-5-methoxy-2-methyl-1-{4-[(trifluoromethyl)thio]benzoyl}-1H-indol-3-yl)acetic acid;
(6-chloro-5-methoxy-2-methyl-1-{4-[(1,1,2,2-tetrafluoroethyl)thio]benzoyl}-1H-indol-3-yl)acetic acid;
(6-chloro-5-methoxy-2-methyl-1-{4-[(pentafluoroethyl)thio]benzoyl}-1H-indol-3-yl)acetic acid; and
[1-(4-cyanobenzoyl)-6-chloro-5-methoxy-2-methyl-1H-indol-3-yl]acetic acid.
[6-fluoro-5-methoxy-2-methyl-1-(thien-2-ylmethyl)-1H-indol-3-yl]acetic acid derivatives having the formula:

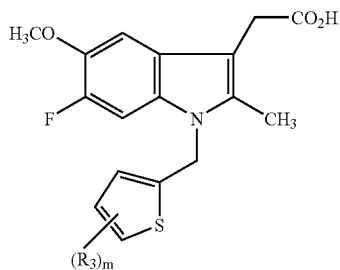

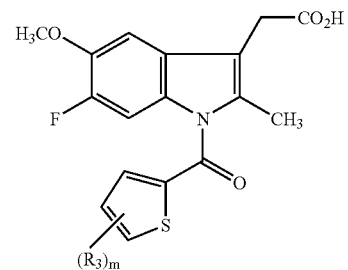

including:

[6-fluoro-5-methoxy-2-methyl-1-(thien-2-ylmethyl)-1H-indol-3-yl]acetic acid;

{6-fluoro-1-[(5-fluorothien-2-yl)methyl]-5-methoxy-2-methyl-1H-indol-3-yl}acetic acid;

{1-[(5-chlorothien-2-yl)methyl]-6-fluoro-5-methoxy-2-methyl-1H-indol-3-yl}acetic acid;

{1-[(5-bromothien-2-yl)methyl]-6-fluoro-5-methoxy-2-methyl-1H-indol-3-yl}acetic acid;

{6-fluoro-5-methoxy-1-[(5-hydroxythien-2-yl)methyl]-2-methyl-1H-indol-3-yl}acetic acid;

{6-fluoro-5-methoxy-1-[(5-methoxythien-2-yl)methyl]-2-methyl-1H-indol-3-yl}acetic acid;

{1-[(5-ethoxythien-2-yl)methyl]-6-fluoro-5-methoxy-2-methyl-1H-indol-3-yl}acetic acid;

(1-{[5-(difluoromethoxy)thien-2-yl]methyl}-6-fluoro-5-methoxy-2-methyl-1H-indol-3-yl)acetic acid;

(6-fluoro-5-methoxy-2-methyl-1-{[5-(trifluoromethoxy)thien-2-yl]methyl}-1H-indol-3-yl)acetic acid;

(6-fluoro-5-methoxy-2-methyl-1-{[5-(pentafluoroethoxy)thien-2-yl]methyl}-1H-indol-3-yl)acetic acid;

(6-fluoro-5-methoxy-2-methyl-1-{[5-(1,1,2,2-tetrafluoroethoxy)thien-2-yl]methyl}-1H-indol-3-yl)acetic acid;

{6-fluoro-5-methoxy-2-methyl-1-[(5-methylthien-2-yl)methyl]-1H-indol-3-yl}acetic acid;

(1-{[5-(difluoromethyl)thien-2-yl]methyl}-6-fluoro-5-methoxy-2-methyl-1H-indol-3-yl)acetic acid;

(6-fluoro-5-methoxy-2-methyl-1-{[5-(trifluoromethyl)thien-2-yl]methyl}-1H-indol-3-yl)acetic acid;

(6-fluoro-5-methoxy-2-methyl-1-{[5-(methylthio)thien-2-yl]methyl}-1H-indol-3-yl)acetic acid;

[1-({5-[(difluoromethyl)thio]thien-2-yl}methyl)-6-fluoro-5-methoxy-2-methyl-1H-indol-3-yl]acetic acid;

[6-fluoro-5-methoxy-2-methyl-1-({5-[(trifluoromethyl)thio]thien-2-yl}methyl)-1H-indol-3-yl]acetic acid;

[6-fluoro-5-methoxy-2-methyl-1-({5-[(pentafluoroethyl)thio]thien-2-yl}methyl)-1H-indol-3-yl]acetic acid;

[6-fluoro-5-methoxy-2-methyl-1-({5-[(1,1,2,2-tetrafluoroethyl)thio]thien-2-yl}methyl)-1H-indol-3-yl]acetic acid; and {1-[(5-cyanothien-2-yl)methyl]-6-fluoro-5-methoxy-2-methyl-1H-indol-3-yl}acetic acid.

[6-fluoro-5-methoxy-2-methyl-1-(thien-3-ylcarbonyl)-1H-indol-3-yl]acetic acid derivatives having the formula:

including:

[6-fluoro-5-methoxy-2-methyl-1-(thien-2-ylcarbonyl)-1H-indol-3-yl]acetic acid;

{6-fluoro-1-[(5-fluorothien-2-yl)carbonyl]-5-methoxy-2-methyl-1H-indol-3-yl}acetic acid;

{1-[(5-chlorothien-2-yl)carbonyl]-6-fluoro-5-methoxy-2-methyl-1H-indol-3-yl}acetic acid;

{1-[(5-bromothien-2-yl)carbonyl]-6-fluoro-5-methoxy-2-methyl-1H-indol-3-yl}acetic acid;

{6-fluoro-5-methoxy-1-[(5-hydroxythien-2-yl)carbonyl]-2-methyl-1H-indol-3-yl}acetic acid;

{6-fluoro-5-methoxy-1-[(5-methoxythien-2-yl)carbonyl]-2-methyl-1H-indol-3-yl}acetic acid;

{1-[(5-ethoxythien-2-yl)carbonyl]-6-fluoro-5-methoxy-2-methyl-1H-indol-3-yl}acetic acid;

(1-{[5-(difluoromethoxy)thien-2-yl]carbonyl}-6-fluoro-5-methoxy-2-methyl-1H-indol-3-yl)acetic acid;

(6-fluoro-5-methoxy-2-methyl-1-{[5-(trifluoromethoxy)thien-2-yl]carbonyl}-1H-indol-3-yl)acetic acid;

(6-fluoro-5-methoxy-2-methyl-1-{[5-(pentafluoroethoxy)thien-2-yl]carbonyl}-1H-indol-3-yl)acetic acid;

(6-fluoro-5-methoxy-2-methyl-1-{[5-(1,1,2,2-tetrafluoroethoxy)thien-2-yl]carbonyl}-1H-indol-3-yl)acetic acid;

{6-fluoro-5-methoxy-2-methyl-1-[(5-methylthien-2-yl)carbonyl]-1H-indol-3-yl}acetic acid;

(1-{[5-(difluoromethyl)thien-2-yl]carbonyl}-6-fluoro-5-methoxy-2-methyl-1H-indol-3-yl)acetic acid;

(6-fluoro-5-methoxy-2-methyl-1-{[5-(trifluoromethyl)thien-2-yl]carbonyl}-1H-indol-3-yl)acetic acid;

(6-fluoro-5-methoxy-2-methyl-1-{[5-(methylthio)thien-2-yl]carbonyl}-1H-indol-3-yl)acetic acid;

[1-({5-[(difluoromethyl)thio]thien-2-yl}carbonyl)-6-fluoro-5-methoxy-2-methyl-1H-indol-3-yl]acetic acid;

[6-fluoro-5-methoxy-2-methyl-1-({5-[(trifluoromethyl)thio]thien-2-yl}carbonyl)-1H-indol-3-yl]acetic acid;

[6-fluoro-5-methoxy-2-methyl-1-({5-[(pentafluoroethyl)thio]thien-2-yl}carbonyl)-1H-indol-3-yl]acetic acid;

[6-fluoro-5-methoxy-2-methyl-1-({5-[(1,1,2,2-tetrafluoroethyl)thio]thien-2-yl}carbonyl)-1H-indol-3-yl]acetic acid; and {1-[(5-cyanothien-2-yl)carbonyl]-6-fluoro-5-methoxy-2-methyl-1H-indol-3-yl}acetic acid.

[6-chloro-5-methoxy-2-methyl-1-(thien-3-ylmethyl)-1H-indol-3-yl]acetic acid derivatives having the formula:

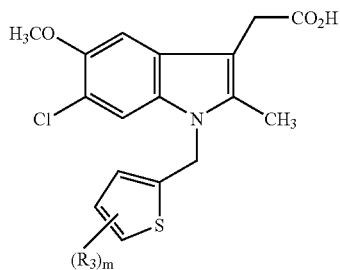

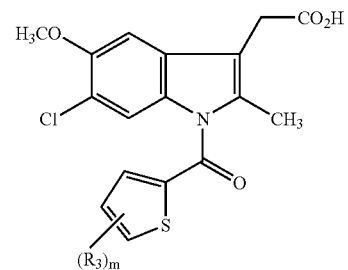

including:

[6-chloro-5-methoxy-2-methyl-1-(thien-2-ylmethyl)-1H-indol-3-yl]acetic acid;

{6-chloro-1-[(5-fluorothien-2-yl)methyl]-5-methoxy-2-methyl-1H-indol-3-yl}acetic acid;

{1-[(5-chlorothien-2-yl)methyl]-6-chloro-5-methoxy-2-methyl-1H-indol-3-yl}acetic acid;

{1-[(5-bromothien-2-yl)methyl]-6-chloro-5-methoxy-2-methyl-1H-indol-3-yl}acetic acid;

{6-chloro-5-methoxy-1-[(5-hydroxythien-2-yl)methyl]-2-methyl-1H-indol-3-yl}acetic acid;

{6-chloro-5-methoxy-1-[(5-methoxythien-2-yl)methyl]-2-methyl-1H-indol-3-yl}acetic acid;

{1-[(5-ethoxythien-2-yl)methyl]-6-chloro-5-methoxy-2-methyl-1H-indol-3-yl}acetic acid;

(1-{[5-(difluoromethoxy)thien-2-yl]methyl}-6-chloro-5-methoxy-2-methyl-1H-indol-3-yl)acetic acid;

(6-chloro-5-methoxy-2-methyl-1-{[5-(trifluoromethoxy)thien-2-yl]methyl}-1H-indol-3-yl)acetic acid;

(6-chloro-5-methoxy-2-methyl-1-{[5-(pentafluoroethoxy)thien-2-yl]methyl}-1H-indol-3-yl)acetic acid;

(6-chloro-5-methoxy-2-methyl-1-{[5-(1,1,2,2-tetrafluoroethoxy)thien-2-yl]methyl}-1H-indol-3-yl)acetic acid;

{6-chloro-5-methoxy-2-methyl-1-[(5-methylthien-2-yl)methyl]-1H-indol-3-yl}acetic acid;

(1-{[5-(difluoromethyl)thien-2-yl]methyl}-6-chloro-5-methoxy-2-methyl-1H-indol-3-yl)acetic acid;

(6-chloro-5-methoxy-2-methyl-1-{[5-(trifluoromethyl)thien-2-yl]methyl}-1H-indol-3-yl)acetic acid;

(6-chloro-5-methoxy-2-methyl-1-{[5-(methylthio)thien-2-yl]methyl}-1H-indol-3-yl)acetic acid;

[1-({5-[(difluoromethyl)thio]thien-2-yl}methyl)-6-chloro-5-methoxy-2-methyl-1H-indol-3-yl]acetic acid;

[6-chloro-5-methoxy-2-methyl-1-({5-[(trifluoromethyl)thio]thien-2-yl}methyl)-1H-indol-3-yl]acetic acid;

[6-chloro-5-methoxy-2-methyl-1-({5-[(pentafluoroethyl)thio]thien-2-yl}methyl)-1H-indol-3-yl]acetic acid;

[6-chloro-5-methoxy-2-methyl-1-({5-[(1,1,2,2-tetrafluoroethyl)thio]thien-2-yl}methyl)-1H-indol-3-yl]acetic acid; and {1-[(5-cyanothien-2-yl)methyl]-6-chloro-5-methoxy-2-methyl-1H-indol-3-yl}acetic acid.

[6-chloro-5-methoxy-2-methyl-1-(thien-2-ylcarbonyl)-1H-indol-3-yl]acetic acid derivatives having the formula:

including:

[6-chloro-5-methoxy-2-methyl-1-(thien-2-ylcarbonyl)-1H-indol-3-yl]acetic acid;

{6-chloro-1-[(5-fluorothien-2-yl)carbonyl]-5-methoxy-2-methyl-1H-indol-3-yl}acetic acid;

{1-[(5-chlorothien-2-yl)carbonyl]-6-chloro-5-methoxy-2-methyl-1H-indol-3-yl}acetic acid;

{1-[(5-bromothien-2-yl)carbonyl]-6-chloro-5-methoxy-2-methyl-1H-indol-3-yl}acetic acid;

{6-chloro-5-methoxy-1-[(5-hydroxythien-2-yl)carbonyl]-2-methyl-1H-indol-3-yl}acetic acid;

{6-chloro-5-methoxy-1-[(5-methoxythien-2-yl)carbonyl]-2-methyl-1H-indol-3-yl}acetic acid;

{1-[(5-ethoxythien-2-yl)carbonyl]-6-chloro-5-methoxy-2-methyl-1H-indol-3-yl}acetic acid;

(1-{[5-(difluoromethoxy)thien-2-yl]carbonyl}-6-chloro-5-methoxy-2-methyl-1H-indol-3-yl)acetic acid;

(6-chloro-5-methoxy-2-methyl-1-{[5-(trifluoromethoxy)thien-2-yl]carbonyl}-1H-indol-3-yl)acetic acid;

(6-chloro-5-methoxy-2-methyl-1-{[5-(pentafluoroethoxy)thien-2-yl]carbonyl}-1H-indol-3-yl)acetic acid;

(6-chloro-5-methoxy-2-methyl-1-{[5-(1,1,2,2-tetrafluoroethoxy)thien-2-yl]carbonyl}-1H-indol-3-yl)acetic acid;

{6-chloro-5-methoxy-2-methyl-1-[(5-methylthien-2-yl)carbonyl]-1H-indol-3-yl}acetic acid;

(1-{[5-(difluoromethyl)thien-2-yl]carbonyl}-6-chloro-5-methoxy-2-methyl-1H-indol-3-yl)acetic acid;

(6-chloro-5-methoxy-2-methyl-1-{[5-(trifluoromethyl)thien-2-yl]carbonyl}-1H-indol-3-yl)acetic acid;

(6-chloro-5-methoxy-2-methyl-1-{[5-(methylthio)thien-2-yl]carbonyl}-1H-indol-3-yl)acetic acid;

[1-({5-[(difluoromethyl)thio]thien-2-yl}carbonyl)-6-chloro-5-methoxy-2-methyl-1H-indol-3-yl]acetic acid;

[6-chloro-5-methoxy-2-methyl-1-({5-[(trifluoromethyl)thio]thien-2-yl}carbonyl)-1H-indol-3-yl]acetic acid;

[6-chloro-5-methoxy-2-methyl-1-({5-[(pentafluoroethyl)thio]thien-2-yl}carbonyl)-1H-indol-3-yl]acetic acid;

[6-chloro-5-methoxy-2-methyl-1-({5-[(1,1,2,2-tetrafluoroethyl)thio]thien-2-yl}carbonyl)-1H-indol-3-yl]acetic acid; and {1-[(5-cyanothien-2-yl)carbonyl]-6-chloro-5-methoxy-2-methyl-1H-indol-3-yl}acetic acid.

[6-fluoro-5-methoxy-2-methyl-1-(thien-3-ylmethyl)-1H-indol-3-yl]acetic acid derivatives having the formula:

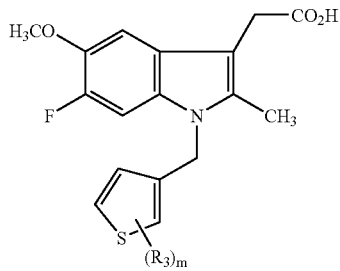

including:

[6-fluoro-5-methoxy-2-methyl-1-(thien-3-ylmethyl)-1H-indol-3-yl]acetic acid;

{6-fluoro-1-[(5-fluorothien-3-yl)methyl]-5-methoxy-2-methyl-1H-indol-3-yl}acetic acid;

{1-[(5-chlorothien-3-yl)methyl]-6-fluoro-5-methoxy-2-methyl-1H-indol-3-yl}acetic acid;

{1-[(5-bromothien-3-yl)methyl]-6-fluoro-5-methoxy-2-methyl-1H-indol-3-yl}acetic acid;

{6-fluoro-5-methoxy-1-[(5-hydroxythien-3-yl)methyl]-2-methyl-1H-indol-3-yl}acetic acid;

{6-fluoro-5-methoxy-1-[(5-methoxythien-3-yl)methyl]-2-methyl-1H-indol-3-yl}acetic acid;

{1-[(5-ethoxythien-3-yl)methyl]-6-fluoro-5-methoxy-2-methyl-1H-indol-3-yl}acetic acid (1-{[5-(difluoromethoxy)thien-3-yl]methyl}-6-fluoro-5-methoxy-2-methyl-1H-indol-3-yl)acetic acid;

(6-fluoro-5-methoxy-2-methyl-1-{[5-(trifluoromethoxy)thien-3-yl]methyl}-1H-indol-3-yl)acetic acid;

(6-fluoro-5-methoxy-2-methyl-1-{[5-(pentafluoroethoxy)thien-3-yl]methyl)-1H-indol-3-yl)acetic acid;

(6-fluoro-5-methoxy-2-methyl-1-{[5-(1,1,2,2-tetrafluoroethoxy)thien-3-yl]methyl}-1H-indol-3-yl)acetic acid;

{6-fluoro-5-methoxy-2-methyl-1-[(5-methylthien-3-yl)methyl]-1H-indol-3-yl}acetic acid (1-{[5-(difluoromethyl)thien-3-yl]methyl}-6-fluoro-5-methoxy-2-methyl-1H-indol-3-yl)acetic acid;

(6-fluoro-5-methoxy-2-methyl-1-{[5-(trifluoromethyl)thien-3-yl]methyl}-1H-indol-3-yl)acetic acid;

(6-fluoro-5-methoxy-2-methyl-1-{[5-(methylthio)thien-3-yl]methyl}-1H-indol-3-yl)acetic acid;

[1-({5-[(difluoromethyl)thio]thien-3-yl}methyl)-6-fluoro-5-methoxy-2-methyl-1H-indol-3-yl]acetic acid;

[6-fluoro-5-methoxy-2-methyl-1-({5-[(trifluoromethyl)thio]thien-3-yl}methyl)-1H-indol-3-yl]acetic acid;

[6-fluoro-5-methoxy-2-methyl-1-({5-[(pentafluoroethyl)thio]thien-3-yl}methyl)-1H-indol-3-yl]acetic acid;

[6-fluoro-5-methoxy-2-methyl-1-({5-[(1,1,2,2-tetrafluoroethyl)thio]thien-3-yl}methyl)-1H-indol-3-yl]acetic acid; and {1-[(5-cyanothien-3-yl)methyl]-6-fluoro-5-methoxy-2-methyl-1H-indol-3-yl}acetic acid.

[6-fluoro-5-methoxy-2-methyl-1-(thien-3-ylcarbonyl)-1H-indol-3-yl]acetic acid derivatives having the formula:

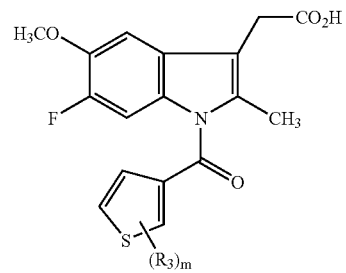

including:

[6-fluoro-5-methoxy-2-methyl-1-(thien-3-ylcarbonyl)-1H-indol-3-yl]acetic acid;

{6-fluoro-1-[(5-fluorothien-3-yl)carbonyl]-5-methoxy-2-methyl-1H-indol-3-yl}acetic acid;

{1-[(5-chlorothien-3-yl)carbonyl]-6-fluoro-5-methoxy-2-methyl-1H-indol-3-yl}acetic acid;

{1-[(5-bromothien-3-yl)carbonyl]-6-fluoro-5-methoxy-2-methyl-1H-indol-3-yl}acetic acid;

{6-fluoro-5-methoxy-1-[(5-hydroxythien-3-yl)carbonyl]-2-methyl-1H-indol-3-yl}acetic acid;

{6-fluoro-5-methoxy-1-[(5-methoxythien-3-yl)carbonyl]-2-methyl-1H-indol-3-yl}acetic acid;

{1-[(5-ethoxythien-3-yl)carbonyl]-6-fluoro-5-methoxy-2-methyl-1H-indol-3-yl}acetic acid;

(1-{[5-(difluoromethoxy)thien-3-yl]carbonyl}-6-fluoro-5-methoxy-2-methyl-1H-indol-3-yl)acetic acid;

(6-fluoro-5-methoxy-2-methyl-1-{[5-(trifluoromethoxy)thien-3-yl]carbonyl}-1H-indol-3-yl)acetic acid;

(6-fluoro-5-methoxy-2-methyl-1-{[5-(pentafluoroethoxy)thien-3-yl]carbonyl}-1H-indol-3-yl)acetic acid;

(6-fluoro-5-methoxy-2-methyl-1-{[5-(1,1,2,2-tetrafluoroethoxy)thien-3-yl]carbonyl}-1H-indol-3-yl)acetic acid;

{6-fluoro-5-methoxy-2-methyl-1-[(5-methylthien-3-yl)carbonyl]-1H-indol-3-yl}acetic acid;

(1-{[5-(difluoromethyl)thien-3-yl]carbonyl}-6-fluoro-5-methoxy-2-methyl-1H-indol-3-yl)acetic acid;

(6-fluoro-5-methoxy-2-methyl-1-{[5-(trifluoromethyl)thien-3-yl]carbonyl}-1H-indol-3-yl)acetic acid;

(6-fluoro-5-methoxy-2-methyl-1-{[5-(methylthio)thien-3-yl]carbonyl}-1H-indol-3-yl)acetic acid;

[1-({5-[(difluoromethyl)thio]thien-3-yl}carbonyl)-6-fluoro-5-methoxy-2-methyl-1H-indol-3-yl]acetic acid;

[6-fluoro-5-methoxy-2-methyl-1-({5-[(trifluoromethyl)thio]thien-3-yl}carbonyl)-1H-indol-3-yl]acetic acid;

[6-fluoro-5-methoxy-2-methyl-1-({5-[(pentafluoroethyl)thio]thien-3-yl}carbonyl)-1H-indol-3-yl]acetic acid;

[6-fluoro-5-methoxy-2-methyl-1-({5-[(1,1,2,2-tetrafluoroethyl)thio]thien-3-yl}carbonyl)-1H-indol-3-yl]acetic acid; and {1-[(5-cyanothien-3-yl)carbonyl]-6-fluoro-5-methoxy-2-methyl-1H-indol-3-yl}acetic acid.

[6-chloro-5-methoxy-2-methyl-1-(thien-3-ylmethyl)-1H-indol-3-yl]acetic acid derivatives having the formula:

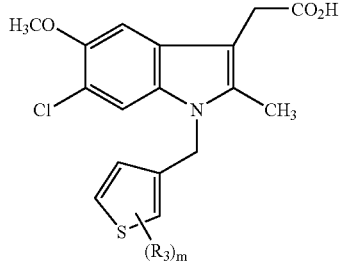

including:

[6-chloro-5-methoxy-2-methyl-1-(thien-3-ylmethyl)-1H-indol-3-yl]acetic acid;
{6-chloro-1-[(5-fluorothien-3-yl)methyl]-5-methoxy-2-methyl-1H-indol-3-yl}acetic acid;
{1-[(5-chlorothien-3-yl)methyl]-6-chloro-5-methoxy-2-methyl-1H-indol-3-yl}acetic acid;
{1-[(5-bromothien-3-yl)methyl]-6-chloro-5-methoxy-2-methyl-1H-indol-3-yl}acetic acid;
{6-chloro-5-methoxy-1-[(5-hydroxythien-3-yl)methyl]-2-methyl-1H-indol-3-yl}acetic acid;
{6-chloro-5-methoxy-1-[(5-methoxythien-3-yl)methyl]-2-methyl-1H-indol-3-yl}acetic acid;
{1-[(5-ethoxythien-3-yl)methyl]-6-chloro-5-methoxy-2-methyl-1H-indol-3-yl}acetic acid
(1-{[5-(difluoromethoxy)thien-3-yl]methyl}-6-chloro-5-methoxy-2-methyl-1H-indol-3-yl)acetic acid;
(6-chloro-5-methoxy-2-methyl-1-{[5-(trifluoromethoxy)thien-3-yl]methyl}-1H-indol-3-yl)acetic acid;
(6-chloro-5-methoxy-2-methyl-1-{[5-(pentafluoroethoxy)thien-3-yl]methyl}-1H-indol-3-yl)acetic acid;
(6-chloro-5-methoxy-2-methyl-1-{[5-(1,1,2,2-tetrafluoroethoxy)thien-3-yl]methyl}-1H-indol-3-yl)acetic acid;
{6-chloro-5-methoxy-2-methyl-1-[(5-methylthien-3-yl)methyl]-1H-indol-3-yl}acetic acid;
(1-{[5-(difluoromethyl)thien-3-yl]methyl}-6-chloro-5-methoxy-2-methyl-1H-indol-3-yl)acetic acid;
(6-chloro-5-methoxy-2-methyl-1-{[5-(trifluoromethyl)thien-3-yl]methyl}-1H-indol-3-yl)acetic acid;
(6-chloro-5-methoxy-2-methyl-1-([5-(methylthio)thien-3-yl]methyl}-1H-indol-3-yl)acetic acid;
[1-({5-[(difluoromethyl)thio]thien-3-yl}methyl)-6-chloro-5-methoxy-2-methyl-1H-indol-3-yl]acetic acid;
[6-chloro-5-methoxy-2-methyl-1-({5-[(trifluoromethyl)thio]thien-3-yl}methyl)-1H-indol-3-yl]acetic acid;
[6-chloro-5-methoxy-2-methyl-1-({5-[(pentafluoroethyl)thio]thien-3-yl}methyl)-1H-indol-3-yl]acetic acid;
[6-chloro-5-methoxy-2-methyl-1-({5-[(1,1,2,2-tetrafluoroethyl)thio]thien-3-yl}methyl)-1H-indol-3-yl]acetic acid; and
{1-[(5-cyanothien-3-yl)methyl]-6-chloro-5-methoxy-2-methyl-1H-indol-3-yl}acetic acid.

[6-chloro-5-methoxy-2-methyl-1-(thien-3-ylcarbonyl)-1H-indol-3-yl]acetic acid derivatives having the formula:

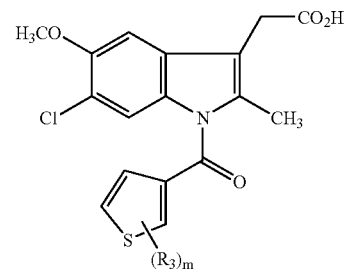

including:

[6-chloro-5-methoxy-2-methyl-1-(thien-3-ylcarbonyl)-1H-indol-3-yl]acetic acid;
{6-chloro-1-[(5-fluorothien-3-yl)carbonyl]-5-methoxy-2-methyl-1H-indol-3-yl}acetic acid;
{1-[(5-chlorothien-3-yl)carbonyl]-6-chloro-5-methoxy-2-methyl-1H-indol-3-yl}acetic acid;
{1-[(5-bromothien-3-yl)carbonyl]-6-chloro-5-methoxy-2-methyl-1H-indol-3-yl}acetic acid;
{6-chloro-5-methoxy-1-[(5-hydroxythien-3-yl)carbonyl]-2-methyl-1H-indol-3-yl}acetic acid;
{6-chloro-5-methoxy-1-[(5-methoxythien-3-yl)carbonyl]-2-methyl-1H-indol-3-yl}acetic acid;
{1-[(5-ethoxythien-3-yl)carbonyl]-6-chloro-5-methoxy-2-methyl-1H-indol-3-yl}acetic acid;
(1-{[5-(difluoromethoxy)thien-3-yl]carbonyl}-6-chloro-5-methoxy-2-methyl-1H-indol-3-yl)acetic acid;
(6-chloro-5-methoxy-2-methyl-1-{[5-(trifluoromethoxy)thien-3-yl]carbonyl}-1H-indol-3-yl)acetic acid;
(6-chloro-5-methoxy-2-methyl-1-{[5-(pentafluoroethoxy)thien-3-yl]carbonyl}-1H-indol-3-yl)acetic acid;
(6-chloro-5-methoxy-2-methyl-1-{[5-(1,1,2,2-tetrafluoroethoxy)thien-3-yl]carbonyl}-1H-indol-3-yl)acetic acid;
{6-chloro-5-methoxy-2-methyl-1-[(5-methylthien-3-yl)carbonyl]-1H-indol-3-yl}acetic acid;
(1-{[5-(difluoromethyl)thien-3-yl]carbonyl}-6-chloro-5-methoxy-2-methyl-1H-indol-3-yl)acetic acid;
(6-chloro-5-methoxy-2-methyl-1-([5-(trifluoromethyl)thien-3-yl]carbonyl}-1H-indol-3-yl)acetic acid;
(6-chloro-5-methoxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-chloro-5-methoxy-2-methyl-1H-indol-3-yl]acetic acid;
[6-chloro-5-methoxy-2-methyl-1-({5-[(trifluoromethyl)thio]thien-3-yl}carbonyl)-1H-indol-3-yl]acetic acid;
[6-chloro-5-methoxy-2-methyl-1-({5-[(pentafluoroethyl)thio]thien-3-yl}carbonyl)-1H-indol-3-yl]acetic acid;
[6-chloro-5-methoxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-6-chloro-5-methoxy-2-methyl-1H-indol-3-yl}acetic acid.

Other compounds within the invention include:

{1-[(5-chlorothien-2-yl)methyl]-5-hydroxy-2-methyl-1H-indol-3-yl}acetic acid

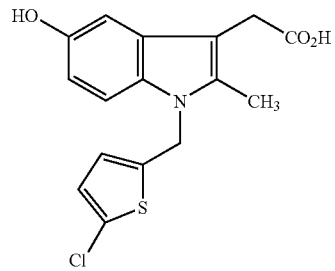

{1-[(5-chlorothien-2-yl)methyl]-5-methoxy-2-methyl-1H-indol-3-yl}acetic acid

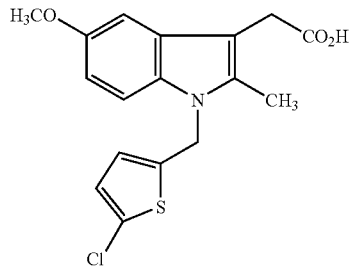

[5-methoxy-1-(4-methoxybenzyl)-2-methyl-1H-indol-3-yl]acetic acid

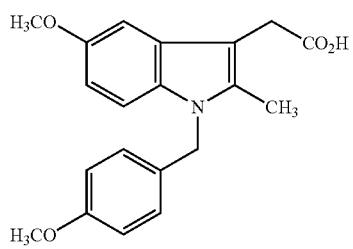

{5-methoxy-2-methyl-1-[4-(trifluoromethoxy)benzyl]-1H-indol-3-yl}acetic acid

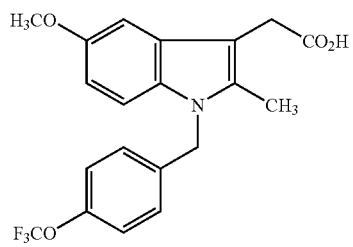

[1-(3-chlorobenzoyl)-5-methoxy-2-methyl-1H-indol-3-yl]acetic acid

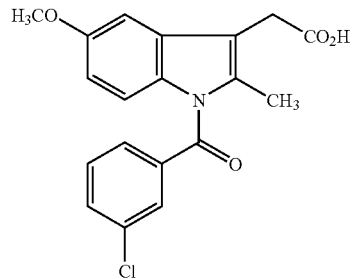

[4-chloro-1-(4-chlorobenzoyl)-5-methoxy-2-methyl-1H-indol-3-yl]acetic acid

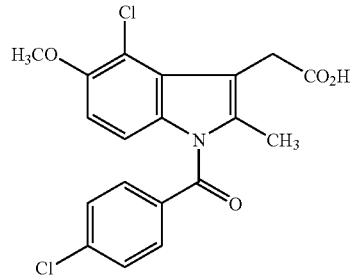

[6-chloro-1-(4-chlorobenzoyl)-5-fluoro-2-methyl-1H-indol-3-yl]acetic acid

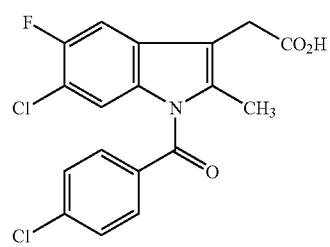

(1-benzyl-5-hydroxy-2-methyl-1H-indol-3-yl)acetic acid

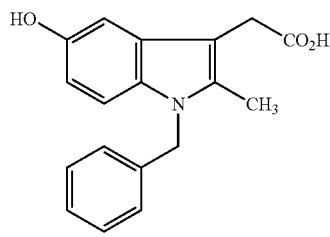

[1-(4-chlorobenzyl)-5-hydroxy-2-methyl-1H-indol-3-yl] acetic acid

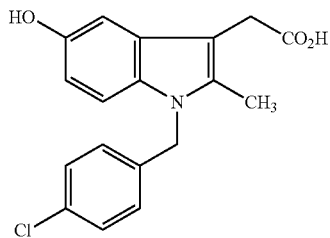

[1-(4-chlorobenzoyl)-5-hydroxy-2-methyl-1H-indol-3-yl] acetic acid

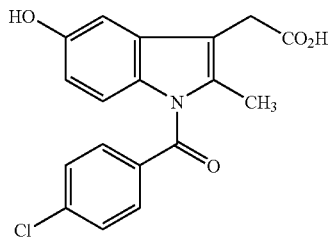

{5-methoxy-2-methyl-1-[4-(trifluoromethoxy)benzoyl]-1H-indol-3-yl}acetic acid

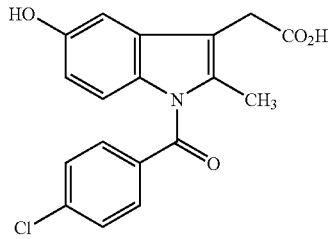

The invention also features compositions comprising a compound having Formula I wherein the composition contains no more than 0.0001%, 0.001%, 0.01%, 0.1%, 0.3%, 0.5%, 0.9%. 1.9%, 5.0%, or 10% by weight other compounds.

In some embodiments the compounds are administered in combination with a second compound useful for preventing and/or treating an allergic reaction or another disease or disorder discussed herein.

The subject can be a mammal, preferably a human. Identifying a subject in need of such treatment can be in the judgment of the subject or a health care professional and can be subjective (e.g., opinion) or objective (e.g., measurable by a test or diagnostic method).

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound that confers a therapeutic effect on the treated subject. The therapeutic effect may be objective (i.e., measurable by some test or marker) or subjective (i.e., subject gives an indication of or feels an effect). An effective amount of the compound described above may range from about 0.05 mg/Kg to about 500 mg/Kg, alternatively from about 1 to about 50 mg/Kg. Effective doses will also vary depending on route of administration, as well as the possibility of co-usage with other agents.

The term "mammal" includes, for example, mice, hamsters, rats, cows, sheep, pigs, goats, horses, monkeys, dogs (e.g., Canis familiaris), cats, rabbits, guinea pigs, and primates, including humans.

The term "prodrug" refers to compounds which are drug precursors which, following administration and absorption, release the drug in vivo through a metabolic process. Exemplary prodrugs include ester and amides of the compounds of Formula I.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$–$C_6$ alkyl indicates that the group may have from 1 to 6 (inclusive) carbon atoms in it (i.e., 1, 2, 3, 4, 5, 6). The term "haloalkyl" refers to an alkyl in which one or more hydrogen atoms are replaced by halo, and includes alkyl moieties in which all hydrogens have been replaced by halo (e.g., perfluoroalkyl).

The terms "arylalkyl" or "aralkyl" refer to an alkyl moiety in which an alkyl hydrogen atom is replaced by an aryl group. Examples of "arylalkyl" or "aralkyl" include benzyl and 9-fluorenyl groups.

The terms "alkylamino" and "dialkylamino" refer to —NH(alkyl) and —N(alkyl)$_2$ radicals respectively. The term "aralkylamino" refers to a —NH(aralkyl) radical. The term "alkoxy" refers to an —O-alkyl radical. The term "mercapto" refers to an SH radical. The term "thioalkoxy" refers to an —S-alkyl radical.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl.

The term "cycloalkyl" as employed herein includes saturated monocyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclopentyl, norbornyl, and adamantyl.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "oxo" refers to an oxygen atom, which forms a carbonyl when attached to carbon, an N-oxide when attached to nitrogen, and a sulfoxide or sulfone when attached to sulfur.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, acyloxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0–2), $S(O)_n$ aryl (where n is 0–2), $S(O)_n$ heteroaryl (where n is 0–2), $S(O)_n$ heterocyclyl (where n is 0–2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The invention includes salts, particularly physiologically acceptable salts, and solvates of the compounds having Formula I. Solvates are forms of the compounds in which the compound forms a complex with solvent molecules by coordination in the solid or liquid states. Hydrates are a special form of solvate in which the compound is coordinated with water.

Some compounds within Formula I may exist in stereoisomeric forms such as enantiomers, diastereomers and mixtures thereof. Mixtures can be separated into stereoisomerically pure constituents.

Some compounds within Formula I may be tautomeric, and the invention encompasses the various tautomeric mixtures.

The details of one or more embodiments of the invention are set forth in the accompanying drawings and the description below. Other features, objects, and advantages of the invention will be apparent from the description and drawings, and from the claims. The patents, patent applications, and publications referenced herein are hereby incorporated by reference in their entirety.

DESCRIPTION OF DRAWINGS

FIG. 1 is a Table that presents data regarding CRTH2 agonist activity, CRTH2 antagonist activity, COX-2 antagonist activity (using two different assays), and COX-1 antagonist activity (using two different assays) for certain compounds. "ND" means not determined and "N/A" means not applicable.

DETAILED DESCRIPTION

Various CRTH2 modulators (e.g., agonists and antagonists) are described herein. Such compounds are useful in the prevention and/or treatment of asthma and other diseases and disorders.

Recruitment and/or activation of eosinophils, basophils and Th2 cells is a prominent feature of the changes that occur in the asthmatic lung. Similar activation of these cell types, or subsets thereof, are believed to play an important role in the etiology of other diseases, including eosinophilic esophagitis and atopic dermatitis (Arora and Yamakazi 2004 *Clin Gastroenterol Hepatol* 2:523–30; Kiehl et al. 2001 *Br J Dermatol* 145:720–729). This fact, combined with the fact that CRTH2 mediates $PGD_2$-induced chemotaxis, suggests that compounds that alter chemotaxis by modulating CRTH2 activity could be useful in controlling chronic airway inflammation, allergic rhinitis, atopic dermatitis, chronic obstructive pulmonary disease (COPD), or eosinophilic esophagitis. Thus, CRTH2 antagonists that reduce the ability of Th2 cells and eosinophils to respond to mast-cell derived PGD2 could be useful for preventing and/or treating allergic disorders such as allergic rhinitis and asthma.

It is often found that agonists induce desensitization of the cell system by promoting internalization and down regulation of the cell surface receptor (*Int Immunol* 15:29–38, 2003). Therefore, certain CRTH2 agonists may be therapeutically useful because they can cause the desensitization of PGD2-responsive cells. It has been shown that certain CRTH2 agonists can induce desensitization of PGD2-responsive cells to subsequent activation by a CRTH2 agonist (see, e.g., Yoshimura-Uchiyama et al. 2004 *Clin Exp Allergy* 34:1283–1290). Importantly, CRTH2 agonists may also cause cross-desensitization. Cross-desensitization, which can occur in many cell-signaling systems, refers to a phenomena whereby an agonist for one receptor can reduce or eliminate sensitivity of a cell type to an unrelated agonist/receptor signaling system. For example, it is known that treatment with the CRTH2 agonist indomethacin reduces expression of CCR3, the receptor for the chemoattractant, eotaxin (Stubbs et al. 2002, *J Biol Chem* 277:26012–26020).

Among the useful antagonists of CRTH2 are compounds having an $IC_{50}$ for CRTH2 of less than about 20, 10, 2.0, 1.5, 1.0, 0.5, 0.4, 0.3, 0.2, 0.1, 0.08, 0.06, 0.04, 0.02, or 0.01 μM. The $IC_{50}$ is judged by inhibition of response to a subsequent 100 nM 15R-methyl Prostaglandin D2 (15-R-methyl-$PGD_2$) treatment in eosinophils. Among the useful agonists of CRTH2 are compounds having an $EC_{50}$ for CRTH2 of less than about 20, 10, 2.0, 1.5, 1.0, 0.5, 0.4, 0.3, 0.2, 0.1, 0.08, 0.06, 0.04, 0.02, or 0.01 μM.

Certain other useful compounds are selective cyclooxygenase-2 (COX-2) inhibitors in addition to being CRTH2 modulators. COX-2 is an inducible and relatively short-lived cyclooxygenase inhibitor, in contrast to cyclooxygenase-1 inhibitor (COX-1). COX-1 is thought to be responsible for maintaining basal level prostaglandin production, which is important for normal gastrointestinal and renal function. COX-2 is induced by certain inflammatory agents, hormones, growth factors, cytokines, and other agents. COX-2 plays a significant role in prostaglandin synthesis within inflammatory cells such as macrophages and monocytes, and prostaglandin production associated with COX-2 induction can have a deleterious effect on the body. Thus, to reduce unwanted inflammation and to treat certain other conditions, it can be desirable to inhibit COX-2 activity without significantly inhibiting COX-1 activity.

Certain of the compounds have no significant ability to inhibit cyclooxygenase-2 (COX-2) at physiological concentrations at which they act as CRTH2 agonists or antagonists. Other of the compounds do not measurably inhibit COX-2 and/or COX-1 at a therapeutically effective dose, e.g., a dose effective to reduce an allergic response, a dose able to attenuate recruitment of eosinophils to a site of contact hypersensitivity, or a dose that reduces the symptoms of an asthmatic attack (e.g., reduction in forced expiratory volume (FEV)).

CRTH2 modulators that are also selective COX-2 inhibitors are those compounds which inhibit COX-2 activity at physiological concentrations where COX-1 activity is not significantly inhibited. Thus, the compounds have an $IC_{50}$ for COX-1 that is at least 2-, 5-, 10-, 15-, 20-, 100-, 500-greater than the $IC_{50}$ for COX-2 as defined by the COX human whole blood assay as described herein. Particularly desirable are compounds that do not significantly inhibit COX-1 at a therapeutically effective concentration, e.g., a concentration effective to reduce pain or inflammation attributable to COX-2 associated prostaglandin production. Useful compounds include those having an $IC_{50}$ for COX-2 of less than about 2.0, 1.5, 1.0, 0.5, 0.4, 0.3, 0.2, 0.1, 0.08, 0.06, 0.04, 0.02, or 0.01 μM, and have an $IC_{50}$ for COX-1 of greater than about 1, 5, 10, 15, 20, 40 or 100 μM. In some embodiments the COX-2 $IC_{50}$ for a compound is less than 20, 10, 5, 3, 2, 1, 0.5, 0.4, 0.3, 0.2, 0.1 or 0.05 times the COX-2 $IC_{50}$ for indomethacin in the same assay. In some embodiments the COX-1 $IC_{50}$ for a compound is at least 2, 5, 10, 25, 50, 100, 500, 1000 or more times the COX-1 $IC_{50}$ for indomethacin in the same assay. In some embodiments, the selectivity for COX-2 over COX-1 for a compound is greater than 3, 5, 10, 50, 100, 200, 500 or 1000 times the selectivity of indomethacin in the same assays.

EXAMPLES

CRTH2 Agonist Assay

CRTH2 agonists increase the expression of CD11b on eosinophils. Neutrophils do not express CRTH2. They do, however, express receptors for other lipid mediators, including 5-oxo-6,8,11,14-eicosatetraenoic acid (5-oxo-ETE), leukotriene B4 (LTB4), and platelet activating factor. Therefore, any increased expression of CD11b by neutrophils is likely to be caused by an activity other than activation of CRTH2. Accordingly, preferred compounds increase CD11b expression on eosinophils, but not on neutrophils.

The potential CRTH2 agonist activity of certain compounds was tested using a CD11b expression assay using essentially the method described by Monneret et al. (*J Pharmacol Exp Ther* 304:349–55, 2003), and the results of this analysis are presented in FIG. 1 where the results of two separate experiments are reported.

Briefly, leukocytes (0.5 ml; $10^6$/ml cells) in PBS containing 0.9 mM $CaCl_2$ and 0.5 mM $MgCl_2$) were incubated with a test compound at room temperature for 10 min. The incubations were terminated by the addition of ice-cold FACSFlow (BD Biosciences; Cat# 342003) and centrifugation (400 g for 5 min at 4° C.). The cells were then incubated for 30 min at 4° C. with a mixture of PE-labeled mouse anti-human VLA-4 (5 µl; BD Biosciences) and FITC-labeled mouse anti-human CD11b (10 µl; Beckman Coulter). The cells were then incubated with Optilyse C (0.25 ml; Beckman Coulter) for 15 min, centrifuged, and then fixed in PBS (0.4 ml; calcium and magnesium free) containing 1% formaldehyde. The distribution of fluorescence intensities among 60,000 cells was measured by flow cytometry. Eosinophils were gated out on the basis of their granularity (high side scatter) and labeling with VLA-4 (PE fluorescence). CD11b was then measured in the eosinophil region on the basis of fluorescence due to FITC. All data were corrected for the value obtained for the corresponding isotype control antibody.

Of the compounds in the Table of FIG. 1, only 5-oxo-ETE increased expression of CD11b on neutrophils. The results presented in FIG. 1 are reported as the $EC_{50}$ in the CD11b expression assay in eosinophils. Compounds with an $EC_{50}$ below 20,000 nM are considered CRTH2 agonists; compounds with an $EC_{50}$ between about 100 nM and about 1,000 nM are considered moderate CRTH2 agonists; and compounds with an $EC_{50}$ below about 100 nM are considered potent agonists. To confirm that the calcium mobilization is caused by inhibition of the CRTH2 receptor certain controls were performed. Accordingly, effect of the compounds on calcium mobilization in neutrophils was tested. If the compound increases calcium mobilization in neutrophils, the mobilization in eosinophils is likely caused by an activity other than inhibition of the CRTH2 receptor. In all cases tested calcium mobilization was only observed in eosinophils.

CRTH2 Antagonist Assay

The potential CRTH2 antagonist activity of certain compounds was tested using an assay that tests the ability of the compounds to block the mobilization of calcium in eosinophils by 15-R-methyl-$PGD_2$ using essentially the method described by Monneret et al. (*J Pharmacol Exp Ther* 304: 349–55, 2003), and the results of this analysis are presented in FIG. 1. A CRTH2 antagonist should block calcium mobilization by subsequently added 15-Methyl-$PGD_2$. The results presented in FIG. 1 are reported as the $IC_{50}$ in the calcium mobilization assay. Compounds with an $IC_{50}$ below 20,000 nM are considered to be CRTH2 antagonists.

The calcium mobilization assay was conducted as follows, adapted from the protocol described by Monneret et al. (*J Pharmacol Exp Ther* 304:349–55, 2003). Leukocytes ($10^7$ cells/ml) were treated with the acetoxymethyl ester of fluo-3 (2 µM; Molecular Probes, Eugene, Oreg.) in the presence of Pluronic F-127 (0.02%; Molecular Probes) for 60 min at 23° C. The mixture was then centrifuged at 200×g for 10 min and the pellet resuspended in PBS to give a concentration of $5 \times 10^6$ cells/ml. The leukocytes were then treated with PC5-labeled mouse anti-human CD16 (3.3 µl/$10^6$ cells; Beckman-Coulter) for 30 min at 0° C. PBS (25 ml) was then added, the mixture centrifuged as described above, and the pellet resuspended in PBS to give a concentration of $3 \times 10^6$ leukocytes/ml. After incubation at 23° C. for 30 min, an aliquot (0.95 ml) of the leukocyte suspension was removed and treated with PBS (50 µl) containing $Ca^{++}$ (36 mM) and $Mg^{++}$ (20 mM). After 5 min, the cells were analyzed by flow cytometry using a FACSCalibur instrument (Becton-Dickinson, San Jose, Calif.). A total of approximately $10^6$ cells were counted over a period of 3 to 4 min for each sample. Fluo-3 fluorescence was measured in eosinophils, neutrophils, and monocytes, which were gated out on the basis of CD16 staining and side scatter. Test compounds were added 2 min after the start of each run followed 2 min later by 15R-Methyl-$PGD_2$. Maximal calcium responses were determined by addition of the calcium ionophore, A23187 (10 µM) one minute after the addition of 15R-Methyl-$PGD_2$.

COX Enzyme Assay

The inhibitory activity of each compound on purified COX-1 and purified COX-2 can be measured using a test kit available from Cayman Chemical (Ann Arbor, Mich.). Because COX-1 and COX-2 convert arachidonic acid to prostaglandin $H_2$ ($PGH_2$), one can assess COX inhibitory activity of a test compound by measuring the effect of the compound on $PGH_2$ production in the presence of purified COX-1 enzyme and in the presence of purified COX-2 enzyme. In this assay, the production of $PGH_2$ can be measured by reducing $PGH_2$ to prostaglandin $F_{2\alpha}$ ($PGF_{2\alpha}$) with $SnCl_2$ and then detecting $PGF_{2\alpha}$ by enzyme immunoassay (EIA) using a suitable antibody. Certain compounds were tested for COX-1 inhibitory activity and for COX-2 inhibitory activity using these purified enzyme assays. The results of this analysis are presented in FIG. 1.

COX Human Whole Blood Assay

A human whole blood assay can also be used to measure the inhibitory activity of compounds on COX-1 and COX-2. Briefly, human whole blood is drawn from 3–6 healthy volunteers who have not taken NSAIDS the previous 2 weeks. To measure COX-1 activity in whole blood, 100 µl of whole blood is combined with a 2 µl aliquot of test compound in vehicle or vehicle alone and incubated for 1 hr at 37° C. as described by Berg et al. (1999 *Inflamm. Res.* 48, 369–379). Serum is isolated from the sample by centrifugation at 12,000 g for 5 min at 4° C. and then assayed for thromboxane B2 (TXB2) levels using an ELISA assay (e.g., Cayman EIA Kit, Catalog Number 519031). To measure COX-2 activity in whole blood, 100 µl of heparinized whole blood is combined with a 1 µl aliquot of 10 mg/ml LPS (lipopolysaccharide) and a 2 µl aliquot of test compound in vehicle or vehicle alone and incubated for 24 h at 37° C. as described by Berg et al. (supra). Serum is isolated from the sample by centrifugation at 12,000 g for 5 min at 4° C. and assayed for prostaglandin $E_2$ ($PGE_2$) using an ELISA assay (e.g., Cayman EIA Kit, Catalog Number 514010). Certain compounds were tested for COX-1 inhibitory activity and for COX-2 inhibitory activity using these human whole blood assays. The results of this analysis are presented in FIG. 1.

Therapeutic Methods

The compounds of the invention that are CRTH2 antagonists can be used, for example, to prevent and/or treat conditions or disorders in which it is considered desirable to reduce or eliminate CRTH2 activity. The compounds of the invention that are CRTH2 agonists can be used, for example, to prevent and/or treat conditions in which it is considered desirable to: (1) downregulate CRTH2 activity via desensitization; (2) downregulate non-CRTH2 chemokine receptor activity via cross-desensitization or (3) shift the balance of Th1 and Th2 cells towards Th2 via agonism at CRTH2. CRTH2 agonists are expected to be especially useful in the prevention and/or treatment of disease and disorders characterized by an imbalance of Th1/Th2 that is shifted towards Th1 cells, e.g., rheumatoid arthritis, Type I diabetes, psoriasis, gastritis, irritable bowel disorder, multiple sclerosis, painless thyroiditis, lupus, and Crohn's Disease.

Compounds that are CRTH2 antagonists or agonists may be used to aid in preventing and/or treating a disease or disorder mediated, regulated or influenced by, for example, Th2 cells, eosinophils, basophils, platelets, Langerhans cells, dendritic cells or mast cells. They also may be used to aid in the prevention or treatment of a disease or disorder mediated, regulated or influenced by $PGD_2$ and metabolites thereof, such as 13,14-dihydro-15-keto-$PGD_2$ and 15-deoxy-Al 2,1'-$PGD_2$.

CRTH2 antagonists are expected to be useful in the prevention and/or treatment of disease and disorders characterized by undesirable activation of Th2 cells, eosinophils, and basophils e.g., asthma, atopic dermatitis, allergic rhinitis, allergies (e.g., food allergies, dust allergies, pollen allergies, mold allergies), and Grave's Disease.

Compounds that are CRTH2 antagonists or agonists may be used to aid in preventing and/or treating the following types of diseases, conditions and disorders:

(1) respiratory tract/obstructive airways diseases and disorders including: acute-, allergic, hatrophic rhinitis or chronic rhinitis (such as rhinitis caseosa, hypertrophic rhinitis, rhinitis puruilenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), antitussive activity, asthma (such as bronchial, allergic, intrinsic, extrinsic and dust asthma particularly chronic or inveterate asthma (e.g. late asthma and airways hyper-responsiveness)), bronchitis (including chronic and eosinophilic bronchitis), chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), chronic obstructive pulmonary disease (COPD)(such as irreversible COPD), chronic sinusitis, conjunctivitis (e.g. allergic conjunctivitis), cystic fibrosis, fanner's lung and related diseases, fibroid lung, hypersensitivity lung diseases, hypersensitivity pneumonitis, idiopathic interstitial pneumonia, nasal congestion, nasal polyposis, otitis media, and chronic cough associated with inflammation or iatrogenic induced;

(2) systemic anaphylaxis or hypersensitivity responses, drug allergies (e.g., to penicillin, cephalosporins), insect sting allergies, and food related allergies which may have effects remote from the gut (such as migraine, rhinitis and eczema);

(3) bone and joint related diseases and disorders including: arthritis including rheumatic, infectious, autoimmune, seronegative, spondyloarthropathies (such as ankylosing spondylitis, psoriatic arthritis and Reiter's disease), osteoarthritis, and systemic sclerosis;

(4) skin and eye related diseases and disorders including: psoriasis, atopical dermatitis, contact dermatitis, other eczmatous, dermitides, seborrheic dermatitis, cutaneous eosinophilias, chronic skin ulcers, cutaneous lupus erythematosus, contact hypersensitivity/allergic contact dermatits (including sensitivity to poison ivy, sumac, or oak), and eosinophilic folliculitis (Ofuji's disease);

(5) gastrointestinal tract related diseases and disorders including: Coeliac disease, cholecystitis, Crohn's disease, enteritis (including eosinophilic gastroenteritis), eosinophilic esophagitis, enteropathy associated with seronegative arthropathies, gastritis, inflammatory bowel disease and irritable bowel disease;

(6) transplant rejection related conditions including: acute and chronic allograft rejection following solid organ transplant, for example, transplantation of kidney, heart, liver, lung, and cornea, chronic graft versus host disease, skin graft rejection, and bone marrow transplant rejection;

(7) inflammation; and (8) other diseases and disorders including: lupus erythematosus; systemic lupus, erythematosus; Hashimoto's thyroiditis, Grave's disease, type I diabetes, eosinophilia fasciitis, hyper IgE syndrome, idiopathic thrombocytopenia pupura; post-operative adhesions, ischemic/reperfusion injury in the heart, brain, peripheral limbs hepatitis (alcoholic steatohepatitis and chronic viral), mastocytosis (cutaneous and systemic), mastitis (mammary gland), vaginitis, vasculitis (e.g., necrotizing, cutaneous, and hypersensitivity vasculitis), myositis (including polyinyositis, derinatomyositis), basophil related diseases including basophilic leukemia and basophilic leukocytosis, and eosinophil related diseases such as Churg-Strauss syndrome.

Administration of Compounds

The compounds of the invention can be administered alone or in combination with other compounds useful in the prevention and/or treatment of diseases and disorders for which compounds of the invention are useful, including any of the diseases or disorders described above. Examples of other therapeutic agents that may be combined with a compound of the invention, either administered separately or in the same pharmaceutical compositions, include, but are not limited to:

inactivating antibodies (e.g., monoclonal or polyclonal) to interleukins (e.g., IL-4 and IL-5 (for example see Leckie et al. 2000 *Lancet* 356:2144));

soluble chemokine receptors (e.g. recombinant soluble IL4 receptor (Steinke and Borish 2001 *Respiratory Research* 2:66));

chemokine receptor modulators including but not limited to antagonists of CCR1 (e.g., CP-481,715 (Gladue et al. *J Biol Chem* 278:40473)), CCR3 (e.g., UCB35625 (Sabroe et al. *J Biol Chem* 2000 275:25985), CCR5 and those described in: WO0039125A1, WO02070523A1, WO03035627A1, WO03084954A1, WO04011443A1; WO04014875A1, WO04018425A1, WO04018435A1, WO04026835A1, WO04026880A1, WO04039376A1, WO04039377A1, WO04039787A1, WO04056773A1, WO04056808A1, and WO04056809A1;

histamine HI receptor antagonists/antihistamines (i.e. any compound that is capable of blocking, inhibiting, reducing or otherwise interrupting the interaction between histamine and its receptor) including but not limited to:—4 astemizole, acrivastine, antazoline, astemizole, azatadine, azelastine, bromopheniramine, carbinoxamine, carebastine, cetirizine, chlorpheniramine, clemastine, cyclizine, cyproheptadine, descarboethoxyloratadine, dexchlorpheniramine, dimethindene, diphenhydramine, diphenylpyraline, doxylamine, ebastine, efletirizine, epinastine, fexofenadine, hydroxyzine, hydroxyzine, ketotifen, levocabastine, levocetirizine, levocetirizine, loratadine, meclizine, mequitazine, methdilazine, mianserin, mizolastine, noberastine, norastemizole, noraztemizole, pheniramine, picumast, promethazine, pyrilamine, temelastine, terfenadine, trimeprazine, tripelenamine, and triprolidin; leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafirlukast, montelukast, montelukast sodium (Singulair®), pranlukast, iralukast, pobilukast, SKB-106,203 and compounds described as having LTD4 antagonizing activity described in U.S. Pat. No. 5,565,473;

PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, W0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

VLA-4 Antagonists;

corticosteroids, such as beclomethasone, methylprednisolone, betamethasone, prednisone, prenisolone, triamcinolone, dexamethasone, fluticasone, flunisolide and hydrocortisone, and corticosteroid analogs such as budesonide;

immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY 1005);

non-steroidal antiinflammatory agents (NSAIDs) such as propionic acid derivatives (e.g., alminoprofen, benoxaprofen, bucloxic acid, carprofen, fenbufen, fenoprofen, flupro-
fen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

cyclooxygenase-2 (COX-2) inhibitors such as celecoxib (Celebrex®), rofecoxib (Vioxx®), valdecoxib, etoricoxib, parecoxib and lumiracoxib;

inhibitors of phosphodiesterase type IV (PDE-IV);

opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat);

anti-diabetic agents such as insulin and insulin mimetics, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®), ciglitazone, pioglitazone (Actos®) and englitazone;

preparations of interferon beta (interferon β-I α, interferon β-I β); gold compounds such as auranofin and aurothioglucose;

TNF inhibitors, e.g., etanercept (Enbrel®), antibody therapies such as orthoclone (OKT3), daclizumab (Zenapax®), basiliximab (Simulec®)), infliximab (Remicade®) and D2E6 TNF antibody;

lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin;

multiple sclerosis therapeutic agents such as interferon β-I β (Betaseron®), interferon β-I α (Avonex®), azathioprine (Imurek®, Imuran®), glatiramer acetate (Capoxone®), a glucocorticoid (e.g., prednisolone) and cyclophosphamide; and other compounds such as 5-aminosalicylic acid and prodrugs thereof DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (ST1571, Gleevec®) and rituximab (Rituxan®).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The agents, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

The agent can be in the form of a pharmaceutically acceptable salt. Such salts are prepared from pharmaceutically acceptable non-toxic bases including inorganic bases and organic bases. Examples of salts derived from inorganic bases include aluminum, ammonium, calcium, copper, ferric, ferrous, lithium, magnesium, manganic salts, manganous, potassium, sodium, zinc, and the like. In some embodiments, the salt can be an ammonium, calcium, magnesium, potassium, or sodium salt. Examples of salts derived from pharmaceutically acceptable organic non-toxic bases include salts of primary, secondary, and tertiary amines, benethamine, N,N'-dibenzylethylenediamine, diethylamine, 2-diethylaminoethanol, 2-dimethylaminoethanol, diethanolamine, ethanolamine, ethylenediamine, N-ethylmorpholine, N-ethylpiperidine, epolamine, glucamine, glucosamine, histidine, hydrabamine, isopropylamine, lysine, methylglucamine, meglumine, morpholine, piperazine, piperidine, polyamine resins, procaine, purines, theobromine, triethylamine, trimethylamine, tripropylamine, and trolamine, tromethamine. Examples of other salts include arecoline, arginine, barium, betaine, bismuth, chlorprocaine, choline, clemizole, deanol, imidazole, and morpholineethanol.

The agents of the invention can be administered orally, e.g., as a tablet or cachet containing a predetermined amount of the active ingredient, pellet, gel, paste, syrup, bolus, electuary, slurry, capsule; powder; granules; as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents of the invention can also be administered by captisol delivery technology, rectal suppository or parenterally.

Compositions of the present invention may also optionally include other therapeutic ingredients, anti-caking agents, preservatives, sweetening agents, colorants, flavors, desiccants, plasticizers, dyes, and the like. Any such optional ingredient must be compatible with the compound of the invention to insure the stability of the formulation.

The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myo-inositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents such as:

BINDERS: corn starch, potato starch, other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch (e.g., STARCH 1500® and STARCH 1500 LM®, sold by Colorcon, Ltd.), hydroxypropyl methyl cellulose, microcrystalline cellulose (e.g. AVICEL™, such as, AVICEL-PH-101™, –103™ and –105™, sold by FMC Corporation, Marcus Hook, Pa., USA), or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, or mixtures thereof, DISINTEGRANTS: agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, or mixtures thereof, LUBRICANTS: calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Plano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, or mixtures thereof.

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly($\epsilon$-caprolactone) and poly(alkylene oxide) (U.S. 20030068384) to create a sustained release formulation. Such formulations can be used to implants that release a compound of the invention or another agent over a period of a few days, a few weeks or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, U.S. 6,180,608, U.S. 20030171296, U.S. 20020176841, U.S. Pat. Nos. 5,672,659, U.S. 5,893,985, U.S. 5,134,122, U.S. 5,192,741, U.S. 5,192,741, U.S. 4,668,506, U.S. 4,713,244, U.S. 5,445,832 U.S. 4,931,279, U.S. 5,980,945, WO 02/058672, WO 97/26015, WO 97/04744, and U.S. 20020019446. In such sustained release formulations microparticles of compound are combined with microparticles of polymer. U.S. Pat. No. 6,011,011 and WO 94/06452 describe a sustained release formulation providing either polyethylene glycols (where PEG 300 and PEG 400 are most preferred) or triacetin. WO 03/053401 describes a formulation which may both enhance bioavailability and provide controlled release of the agent within the GI tract. Additional controlled release formulations are described in WO 02/38129, EP 326 151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasally using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-powder inhalers (DPIs)) can also be used in intranasal applications. Aerosol formulations are stable dispersions or suspensions of solid material and liquid droplets in a gaseous medium and can be placed into pressurized acceptable propellants, such as hydrofluroalkanes (HFAs, i.e. HFA-134a and HFA-227, or a mixture thereof), dichlorodifluoromethane (or other chlorofluocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants, which include but are not limited to bile salts and those described in U.S. Pat. No. 6,524,557 and references therein. The surfactants described in U.S. Pat. No. 6,524,557, e.g., a C8–C16 fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. Nos. 5,230,884, U.S. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. Nos. 5,348,730, U.S. 6,436,367, WO 91/04011, and U.S. Pat. Nos. 6,294,153 and U.S. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's *The Science and Practice of Pharmacy*. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be fused to immunoglobulins or albumin, or incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, *Nature Reviews Drug Discovery* 2: 214–221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

The agents can be a free acid or base, or a pharmacologically acceptable salt thereof. Solids can be dissolved or dispersed immediately prior to administration or earlier. In some circumstances the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). The formulations may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Pharmaceutical agents can be sterilized by filter sterilization or by other suitable means.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's *Pharmaceutical Sciences*, 18th Ed., Mack Publishing Company, 1995.

Methods to increase chemical and/or physical stability of the agents the described herein are found in WO 00/04880, and WO 97/04796 and the references cited therein.

Methods to increase bioavailability of the agents described herein are found in U.S. 20030198619, WO 01/49268, WO 00/32172, and WO 02/064166. Glycyrrhizinate can also be used as an absorption enhancer (see, e.g., EP397447). WO 03/004062 discusses *Ulex europaeus* I (UEA1) and UEAI mimetics which may be used to target the agents of the invention to the GI tract. The agents described herein and combination therapy agents can be packaged as a kit that includes single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation.

A number of embodiments of the invention have been described. Nevertheless, it will be understood that various modifications may be made without departing from the spirit and scope of the invention.

What is claimed is:

1. A compound having the formula:

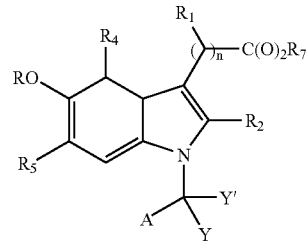

wherein:

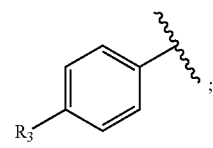

R is H, a $C_1$–$C_3$ alkyl, optionally independently substituted with one or more halogen;

$R_1$ is H; a $C_1$–$C_6$ alkyl, optionally independently substituted with one or more —OH, —$NH_2$, or halogen; or a $C_2$–$C_6$ alkenyl optionally independently substituted with one or more —OH, —$NH_2$ or halogen;

$R_2$ is a $C_1$–$C_6$ alkyl, optionally independently substituted with one or more halogen; or a $C_2$–$C_6$ alkenyl optionally independently substituted with one or more halogen;

$R_3$ is a halogen; —CN; —OH; —SH; a $C_2$–$C_3$ alkyl, optionally independently substituted with one or more halogen; —$OR_{3A}$; —$SR_{3A}$; —$SOR_{3A}$; or —$S(O)_2R_{3A}$, wherein $R_{3A}$ is a $C_1$–$C_3$ alkyl, optionally independently substituted with one or more halogen;

m is 1, 2, 3, 4 or 5;

$R_4$ is H or a halogen;

$R_5$ is a halogen;

Y and Y' are both H; and $R_7$ is $R_{7A}$, wherein $R_{7A}$ is: H or a $C_1$ to $C_6$ alkyl, alkenyl, alkynyl, aryl, cycloalkyl, or arylalkyl optionally independently substituted with one or more halogen —OH, —C(O)OH, or —$NH_3$.

2. The compound of claim 1 wherein m is 1.

3. The compound of claim 1 wherein m is 2.

4. The compound of claim 1 wherein m is 3.

5. The compound of claim 1 wherein $R_3$ is F; Cl; —CN; —OH; —SH; a $C_2$–$C_3$ alkyl, optionally independently substituted with one or more F or Cl; —$OR_{3A}$; —$SR_{3A}$; —$SOR_{3A}$; or —$S(O)_2R_{3A}$, wherein $R_{3A}$ is a $C_1$–$C_3$ alkyl, optionally independently substituted with one or more F or Cl.

6. The compound of claim 5 wherein $R_3$ is F; Cl; —CN; —OH; —SH; or a $C_2$–$C_3$ alkyl, optionally independently substituted with one or more F or Cl.

7. The compound of claim 5 wherein $R_3$ is —$OR_{3A}$; —$SR_{3A}$; —$SOR_{3A}$; or —$S(O)_2R_{3A}$, wherein $R_{3A}$ is a $C_1$–$C_3$ alkyl, optionally independently substituted with one or more F or Cl.

8. The compound of claim 1 wherein R is H.

9. The compound of claim 1 wherein R is a $C_1$–$C_3$ alkyl, optionally independently substituted with one or more halogen.

10. The compound of claim 1 wherein $R_4$ is H, F or Cl.

11. The compound of claim 1 wherein $R_5$ is F or Cl.

12. The compound of claim 1 wherein R is H, or a $C_1$–$C_3$ alkyl, optionally independently substituted with one or more F or Cl.

13. The compound of claim 1 wherein $R_1$ is H; a $C_1$–$C_6$ alkyl, optionally independently substituted with one or more —OH, —$NH_2$, F or Cl; or a $C_2$–$C_6$ alkenyl optionally independently substituted with one or more —OH, —$NH_2$, F or Cl.

14. The compound of claim 1 wherein $R_2$ is H; a $C_1$–$C_6$ alkyl, optionally independently substituted with one or more F or Cl; or a $C_2$–$C_6$ alkenyl optionally independently substituted with one or more F or Cl.

15. The compound of claim 1 wherein any halogen is selected from F and Cl.

16. The compound of claim 1 wherein $R_3$ is selected from: F, Cl, Br, OH, —$OCH_3$, —$OCH_2CH_3$, —$OCF_2H$, —$OCF_3$, —$OCF_2CF_3$, —$OCF_2CF_2H$, —$CH_3$, —$CF_2H$, —$CF_3$, —$SCH_3$, —$SCF_2H$, —$SCF_3$, —$SCF_2CF_3$, —$SCF_2CF_2H$, and —CN.

17. A pharmaceutical composition comprising the compound of claim 1 and a pharmaceutically acceptable carrier.

* * * * *

UNITED STATES PATENT AND TRADEMARK OFFICE
CERTIFICATE OF CORRECTION

PATENT NO.        : 7,205,329 B2
APPLICATION NO.   : 11/183626
DATED             : April 17, 2007
INVENTOR(S)       : Yueh-Tyng Chien et al.

It is certified that error appears in the above-identified patent and that said Letters Patent is hereby corrected as shown below:

In claim 1, column 48, replace the first formula with:

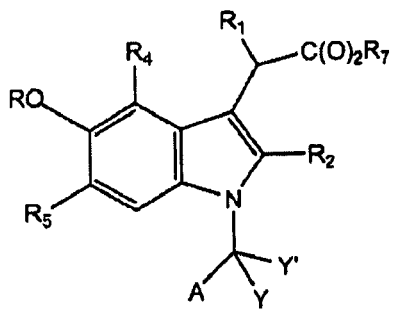

In claim 1, column 48, replace the second formula with:

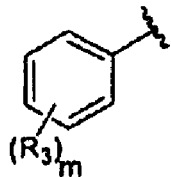

In claim 16, column 50, line 30, delete "—$CH_3$, —$CF_2H$, —$CF_3$"

Signed and Sealed this

Ninth Day of September, 2008

JON W. DUDAS
*Director of the United States Patent and Trademark Office*